(12) United States Patent
Werner et al.

(10) Patent No.: US 6,994,985 B1
(45) Date of Patent: Feb. 7, 2006

(54) DEVELOPMENT OF ANTI-SIGMA FACTOR AGENTS

(75) Inventors: Milton H. Werner, New York, NY (US); Lester J. Lambert, New York, NY (US)

(73) Assignee: Rockefeller University, New York, NY (US)

(*) Notice: Subject to any disclaimer, the term of this patent is extended or adjusted under 35 U.S.C. 154(b) by 436 days.

(21) Appl. No.: 10/299,732

(22) Filed: Nov. 18, 2002

Related U.S. Application Data

(60) Provisional application No. 60/332,446, filed on Nov. 16, 2001.

(51) Int. Cl.
*C12Q 1/18* (2006.01)
*C12Q 1/00* (2006.01)
*C12N 1/00* (2006.01)

(52) U.S. Cl. .............................. 435/32; 435/4; 435/29; 435/849

(58) Field of Classification Search ................. 435/32, 435/4, 29, 849

See application file for complete search history.

(56) References Cited

OTHER PUBLICATIONS

Lambert et al, EMBO J., Dec. 2001; V.20(24): p 7149-7159.*
Guerra et al; Antimicrobial Agents & Chemotherapy, Apr. 2001, p. 1305-1308, V. 45(4).*
Urbauer, Jeffrey L. et al. (2002) "Solution structure and stability of anti-sigma factor AsiA: Implications for novel functions" vol.: 99, No. 4, pp. 1831-1835.

* cited by examiner

*Primary Examiner*—Louise N. Leary
(74) *Attorney, Agent, or Firm*—Klauber & Jackson

(57) ABSTRACT

Sigma factors are a unique family of essential proteins found in bacterial, but not eukaryotic cells, which are responsible for recognition of promoter DNA and delivery of the catalytic domain of RNA polymerase to a gene signaled to be expressed. The present invention relates to methods for identifying agents that are capable of inhibiting bacterial gene expression via inhibition of sigma factor activity. In particular, the invention relates to the interaction of bacteriophage T4 AsiA protein and the C-terminal DNA binding domain of sigma factor (the SR4 domain) and the use of the structural information derived from this interaction to model, prepare and identify agents capable of binding and inhibiting sigma factor activity. Moreover, the invention relates to the design of AsiA mimics, including small organic molecules, peptides or proteins that binds SR4 and abrogates sigma factor activity, or screening for AsiA mimics that show bacteriostatic or bacteriocidal properties.

12 Claims, 12 Drawing Sheets

FIG. 8

| ID | start | sequence | end |
|---|---|---|---|
| 15735 | 533 | DSATTESLRAATHDVLAGLTA REAKVLRMRFGIDMNTDHTLEEVGKQFDVTRERIRQIEAKALRKLRHP SRSEVLRSFLDD | 613 |
| 24323896 | 521 | .....S......S......S............K..........S................................. | 601 |
| 15616680 | 532 | .....S......S......S.............................I........................... | 612 |
| 15803609 | 533 | ............................................................................. | 613 |
| 16761985 | 580 | ............................................................................. | 660 |
| 16766511 | 580 | ............................................................................. | 660 |
| 10720030 | 523 | ............................................................................. | 603 |
| 22127411 | 552 | .....S......S......S........................................................ | 632 |
| 133311 | 535 | ............................................................................. | 615 |
| 216672345 | 537 | .....S......S......S.........E................................................ | 617 |
| 16120968 | 532 | .....S......S......S............................................................ | 612 |
| 147756 | 533 | ...............................................Y............................. | 613 |
| 16130963 | 533 | ...............................................Y............................. | 613 |
| 23428541 | 532 | .....S...S..KS......E............................................I............ | 612 |
| 24372864 | 536 | .....S..G...N.......E............................................I.K......E | 616 |
| 7388082 | 534 | ........S...........................................X......................... | 614 |
| 1173127 | 135 | ............................................................................. | 215 |
| 16272477 | 549 | ....AQ..KV..E..E...P............................................T......E | 629 |
| 15640541 | 545 | ....AT..K...R...P............................................................ | 625 |
| 15603106 | 542 | ....AQ..KV..E..E...P............................................T......E | 622 |

DEVELOPMENT OF ANTI-SIGMA FACTOR AGENTS

CROSS-REFERENCE TO RELATED APPLICATIONS

The present application is a non-provisional application claiming the priority of provisional application Ser. No. 60/332,446, filed Nov. 16, 2001, now abandoned, the disclosure of which is incorporated by reference herein in its entirety. Applicants claim the benefits of this application under 35 U.S.C. §119 (e).

GOVERNMENT SUPPORT

This work was funded, at least in part, by the U.S. Public Health Service, National Institutes of Health, grant GM63793. The government may have certain rights to the invention.

FIELD OF THE INVENTION

The present invention is directed to methods for identification of agents capable of inhibiting or altering bacterial gene transcription. Moreover, the present invention provides for methods useful in the identification of anti-sigma factor agents having bacteriocidal or bacteriostatic properties.

BACKGROUND OF THE INVENTION

The development of anti-microbial agents necessitates the discrimination of the host organism from that of the invading pathogen. To achieve this end, unique features of the pathogen are logically targeted by the anti-microbial agent. There is an ongoing need for the identification and development of novel anti-microbial agents having specificity for the target pathogen, without exhibiting toxicity to the host organism.

Bacteriophage T4 development within *E. coli* is regulated by a controlled program of transcriptional activation and repression (Mosig & Hall, 1994, *Molecular Biology of Bacteriophage T4*, pp. 127–131; Sanson & Uzan, 1995, FEMS Microbiol. Rev. 17: 141–150). Within a few minutes after infection, the host RNA polymerase (RNAP) holoenzyme ($E\sigma^{70}$) transcribes several early genes of the bacteriophage genome that encode proteins capable of blocking host replication, transcription and translation. To redirect the host $E\sigma^{70}$ to transcribe T4 gene products, $E\sigma^{70}$ is modified through both covalent ADP-ribosylation of the α subunits and through binding of phage encoded proteins to the $E\sigma^{70}$ (Stitt & Hinton, 1994, *Molecular Biology of Bacteriophage T4*, pp. 142–160). Whereas expression of early T4 genes relies on unmodified polymerase, gene expression later in the life cycle requires a modified $E\sigma^{70}$ to effectively transcribe T4 genes.

AsiA, an early gene product, is necessary to ensure the progression of transcription from the T4 early to middle genes. AsiA is a small protein (10.6 kD) whose amino acid sequence is unrelated to any other protein in either the prokaryotic or eukaryotic sequence databases (Orsini et al., 1993, J. Bact. 175: 85–93). AsiA strongly represses transcription from host promoters in vitro (Stevens, 1976, *RNA Polymerase*, pp. 617–627; Orsini et. al., 1993, J. Bact. 175-85–93), although AsiA probably acts in tandem with other phage encoded factors to achieve complete repression of host gene expression in vivo (Pene & Uzan, 2000, Mol. Microbiol. 35: 1180–1191). AsiA additionally functions as a co-activator for phage middle gene expression in conjunction with the T4 MotA protein (Ouhammouch et al., 1995, PNAS 92: 1451–1455; Hinton, et al., 1996, Methods Enzymol. 274: 43–57). These dual regulatory events with opposing transcriptional consequences are the result of specific binding between AsiA and host $E\sigma^{70}$ wherein AsiA interacts with the C-terminal conserved domain of $\sigma^{70}$ (termed region 4 (SR4)) (Severinova et al., 1996, J. Mol. Biol. 263: 637–647; Adelman, et al., 1997, J. Biol. Chem. 272: 27435–27443; Pahari & Chatterji, 1997, FEBS Letters 411: 60–62; Colland et al., 1998, Mol. Microbiol. 27: 819–829; Severinova et al., 1998, J. Mol. Biol. 279: 9–18; Sharma et al., 1999, J. Mol. Biol. 290: 905–915; Minakhin et al., 2001, J. Mol. Biol. 306: 631–642). Genetic and biochemical experiments have suggested that AsiA interacts with SR4 in a 1:1 complex (Adelman, et al., 1997, J. Biol. Chem. 272: 27435–27443). The interaction with SR4 most likely occurs with at least a portion of the putative DNA-recognition helix of SR4 (Pahari & Chatterji, 1997, FEBS Letters 411: 60–62; Colland et al., 1998, Mol. Micobiol. 27: 819–829; Severinova et al., 1998, J. Mol. Biol. 279: 9–18; Minakhin et al, 2001, J. Mol. Biol. 306: 631–642). AsiA is capable of tightly associating with SR4 in the presence or absence of core RNAP (Severinova et al., 1996, J. Mol. Biol. 263: 637–647; Adelman, et al., 1997, J. Biol. Chem. 272: 27435–27443; Pahari & Chatterji, 1997, FEBS Letters 411: 60–62; Colland et al., 1998, Mol. Microbiol. 27: 819–829; Severinova et al., 1998, J. Mol. Biol. 279: 9–18) and there may be a preferential association with free $\sigma^{70}$ in order to establish the full repressive effect of AsiA on host gene expression (Hinton & Vuthoori, 2000, J. Mol. Biol. 304: 731–739). The consequence of AsiA interaction with SR4 is to block the formation of closed $E\sigma^{70}$ complexes at host promoters which harbor the two conserved $\sigma^{70}$ DNA binding elements centered at −10 and −35. At T4 middle promoters, the $\sigma^{70}$ −35 binding element is replaced with a binding site for MotA centered at −30. The presence of a MotA/DNA complex preferentially recruits AsiA-modified $E\sigma^{70}$ to T4 middle promoters to specifically transcribe these genes.

It is toward a better understanding of modeling and identification of anti-sigma factor agents of various bacterial species that the present invention is directed, based upon the precise definition acquired from the nature of the interactions between AsiA and the SR4 domain of $E\sigma^{70}$ as derived from the studies herein.

SUMMARY OF THE INVENTION

In its broadest aspect, the present invention is directed to methods for identifying agents capable of inhibiting bacterial gene transcription and thus exhibiting bacteriocidal or bacteriostatic activity. The method is based on the identification by the inventors herein of the structure of the bacteriophage T4 AsiA protein, its naturally-occurring dimers, and the interface between the SR4 domain of $E\sigma^{70}$ (herein referred to interchangeably as sigma or sigma factor) and AsiA protein in an SR4/AsiA heterodimer, the specific sites of interaction between these interacting proteins, and using these sites of interaction to model, prepare and identify agents capable of binding to SR4 and inhibiting sigma factor activity. Such agents may be designed to mimic AsiA or its particular binding sites on SR4, and may be a protein, a peptide, or a small-molecule compound, such as an organic compound, that binds to SR4 and abrogates sigma activity, or at least alters the spectrum of promoters recognizable by the antagonized SR4 to disrupt normal bacterial gene transcription to render cells nonviable or unable to reproduce. AsiA may serve as the starting point in designing such AsiA mimetics (also referred to herein as SR4 antagonists) for a particular bacterial species, or for improving the activity of a small-molecule SR4 antagonist compound in any species. Such compounds may include proteins or peptides derived from or based on the amino acid sequence of AsiA or fragments of AsiA, the compounds having one or more alterations, deletions, or other changes in the amino acid sequence of AsiA or fragments of AsiA which cause an increase in its binding to SR4. Preferably, the AsiA mimetic is a small organic molecule. This process may be applied to any bacterial species for which an inhibitor of gene transcription is desired.

In a particular and non-limiting embodiment of the invention, a target bacterial species is selected for which an inhibitor of bacterial gene transcription is desirably identified. The sites of interaction described identified herein between AsiA and SR4 of *E. coli* is used as a basis to identify the sites on the SR4 domain of the target species' sigma factor that would be sites for interaction with AsiA and thus inhibiting sigma factor activity in the target species. Since the sigma factor target represents a domain with highly conserved amino acid sequence in all bacteria (FIG. 8), the efficacy of the AsiA/SR4 interaction will remain intact regardless of the bacterial source. These identified sites can then be used to model a modified AsiA protein that specifically binds to the target species sigma and inhibits gene transcription. These identified sites may also be used to identify peptides as well as small-molecule compounds also capable of interacting with the corresponding sites in the target species SR4 domain of sigma and inhibiting sigma activity.

In another embodiment, the identified sites of interaction between *E. coli* SR4 and AsiA may be used as the starting point to prepare mutant proteins related to AsiA with altered and preferably improved binding properties to SR4, which may be used to inhibit bacterial gene transcription or preferably serve as the basis for the modeling and design of small-molecule antibiotic agents. In particular, portions of helices H1 and H3 of AsiA comprise sites of interactions with SR4 and are sites for modification to increase affinity. In a further embodiment, about the first 40 amino acid residues, and more particularly, amino acids 3–20 and 33–44 of AsiA have been identified as sites of interaction between AsiA and SR4, and are thus preferred amino acid residue targets for modification in order to prepare a SR4 antagonist capable of disrupting bacterial gene expression. Even more particularly, Asp 6, Glu 10, Ile 11, Ile 12, Thr 13, Leu 18, Ala 35, Phe 36, Glu 39, and Ile 40 of AsiA are sites of interaction between AsiA and SR4 and are thus sites to be taken into account in the design of SR4 antagonists of other bacterial species or for increasing the antagonistic activity of AsiA.

Screening of compounds for ability to antagonize sigma activity and in particular bind to the SR4 domain of sigma may be carried out in accordance with the present invention. In one aspect, the ability of an agent to compete with the binding between a fragment of AsiA comprising about the first 40 amino acid residues of AsiA, or more particularly, amino acids 3–20 and 33–44 of AsiA, or even more particularly, any one or a combination of Asp 6, Glu 10, Thr 13, Leu 18, Ala 35, Phe 36, Glu 39, Ile 11, Ile 12 and Ile 40 of AsiA are sites of interaction between AsiA and SR4 that may be used in an assay for agents of the invention which are inhibitors of bacterial gene transcription.

These assays may include NMR 'footprinting' in which the effects of inhibitors of bacterial gene expression are followed based on their capacity to interact with SR4.

These and other aspects of the invention will be appreciated from consideration of the following brief description of the figures and the ensuing detailed description of the invention.

DESCRIPTION OF THE FIGURES

The patent or application file contains at least one drawing executed in color.

FIG. 8: Representative sequence alignment of SR4 domains from 20 randomly chosen eubacteria (SEQ ID NO: 1). The alignment was produced using the ENTREZ server at the NCBI website in the National Library of Medicine. The SR4 sequence of *Eschericia coli* sigma70 is shown at the top and the GeneBank accession number is given in the first column of the figure. Identical residues are shown by periods, with only the differences in the randomly chosen set indicated using single letter amino-acid codes. The box at the top of the figure indicates the segment of SR4 which contains the amino acid residues which contact AsiA. As is readily apparent, SR4 domains are greater than 90% identical in all eubacteria.

DETAILED DESCRIPTION OF THE INVENTION

Figure 1:
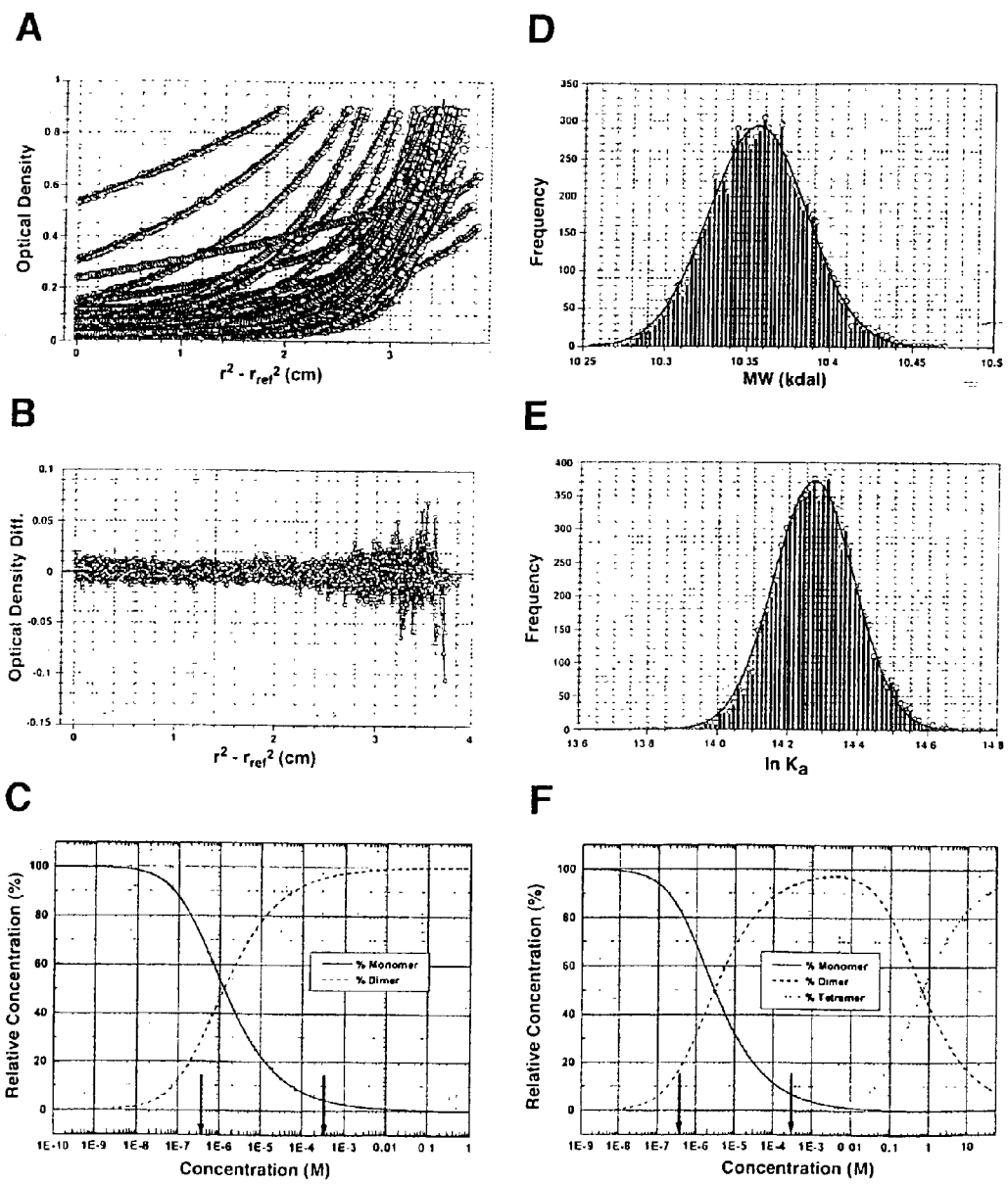
FIG. 1: Sedimentation equilibrium analysis of the AsiA dimer. A) Overlay of 38 wavelength scans and B) residuals from the global fit of the data as described under Methods. The Monte Carlo distribution of the molecular weight (C) and the association constant (D) (in $K_a$) are shown which establish an experimental $M_r=10.36\pm0.077$ kD for the monomer and an association constant of $1.58\pm0.404\times10^6 M^{-1}$. The equilibrium distribution plots for monomer-dimer (E) and monomer-dimer-tetramer (F) fits reveal that very little tetramer was present at the concentrations at which these measurements were taken (indicated by vertical arrows) and result in low confidence in the monomer-tetramer association constant.

In the present application, it is argued that an efficient repressor of bacterial gene expression could serve as a model to develop unique antibiotic agents which are efficacious in a human host. This repressor, the T4 bacteriophage AsiA protein, is capable of repressing the expression of homeostatic genes in a bacterium quantitatively, leading to the death of the bacterial host invaded by the bacteriophage. The target of AsiA is the DNA recognition subunit of RNA polymerase, a protein known as $\sigma^{70}$. $\sigma^{70}$ is responsible for delivering the catalytic domain of RNA polymerase to a target gene that is to be transcribed. The structure of $\sigma^{70}$ is unique to bacteria (Campbell et al 2002, Mol. Cell 9, 527–539; Groft et al 1998, Proc. Natl. Acad. Sci. USA 95, 9117–9122), thus, AsiA is incapable of repression of gene expression in a eukaryotic host. AsiA acts by modification of the host RNA polymerase holoenzyme, binding to conserved region 4 (SR4) of $\sigma^{70}$ and suppressing $\sigma^{70}$'s ability to recruit holoenzyme to its target promoters and thereby to express target genes. Based thereon, methods are provided for modeling, identifying and preparing anti-sigma factor mimics applicable to various microbial species providing bacteriostatic and bacteriocidal compounds for use in the treatment of infections. Infections include bacterial infections which affect plants and animals, preferably mammalian animals, and most preferably, humans, but it is not so limiting. Compounds identified by the methods herein may be delivered to the bacteria by administration of a pharmaceutical compositions comprising an agents of the invention, by conventional means and routes, for effective treatment.

Non-limiting examples of bacterial pathogens against which agents identified by the methods of the invention may be used for control include the plant pathogens such as *Erwinia amylovora, Clavibacter michiganense, Erwinia carotovora, Pseudomonas solanacearum, Pseudomonas syringae,* and *Xanthomonas* spp. including *campestris* pv. *vesicatoria*, as non-limiting examples, and animal pathogens, particularly human pathogens, such as but not limited to *Escherichia coli, Staphylococcus aureus, Streptococcus pyogenes, Bacillus anthracis, Klebsiella pneumoniae, Mycobaterium tuberculosis, Mycobacterium leprae, Vibrio cholerae, Neisseria gonorrhoeae, Treponema pallidum, Pseudomonas aeruginosa, Leigonella* spp., *Yersinia pestis, Bordetella pertussis, Salmonella* spp., *Clostridium tetani* and other species, *Shigella dysinteriae*, and *Corynebacterium diphtheriae*.

Preferably, the methods of the invention are used to identify small-molecule compounds capable of penetrating a bacterial cell, interacting with the SR4 domain of sigma, and altering the normal promoter-interacting site of sigma resulting in lack of bacterial growth or death of the bacterial cell. The present invention embraces compounds identified by carrying out the methods of the invention.

In the practice of the present invention, based on structure of the bacteriophage T4 AsiA protein, its naturally-occurring dimers, and the interface between the SR4 domain of E$\sigma^{70}$ (herein referred to interchangeably as sigma or sigma factor) and AsiA protein in an SR4/AsiA heterodimer, and the specific sites of interaction between these interacting proteins (described hereinbelow), these data are used to model, prepare and identify agents capable of binding to SR4 and inhibiting sigma factor activity. Such agents may be designed to mimic AsiA or its particular binding sites on SR4, and may be a protein, a peptide, or a small-molecule compound, such as an organic compound, that binds to SR4 and abrogates sigma activity, or at least alters the spectrum of promoters recognizable by the antagonized SR4 to disrupt normal bacterial gene transcription to render cells nonviable or unable to reproduce. AsiA may serve as the starting point in designing such AsiA mimetics (also referred to herein as SR4 antagonists) for a particular bacterial species, or for improving the activity of a small-molecule SR4 antagonist compound in any species. Such compounds may include proteins or peptides derived from or based on the amino acid sequence of AsiA or fragments of AsiA, the compounds having one or more alterations, deletions, or other changes in the amino acid sequence of AsiA or fragments of AsiA which cause an increase in its binding to SR4. Preferably, the AsiA mimetic is a small organic molecule. This process may be applied to any bacterial species for which an inhibitor of gene transcription is desired.

For example, a target bacterial species is selected for which an inhibitor of bacterial gene transcription is desirably identified, such as *Mycobacterium tuberculosis*. The sites of interaction described and identified herein between AsiA and SR4 of *E. coli* is used as a basis to identify the sites on the SR4 domain of the *M. tuberculosis* sigma factor that would be sites for interaction with AsiA and thus inhibiting sigma factor activity in this bacterial species. These identified sites are then used to model a modified AsiA protein that specifically binds to the target species sigma and inhibits or alters gene transcription. In an intermediate step, a modified AsiA protein molecule tailored to the specific SR4 sites of the target bacterium may be prepared and the correct interaction corroborated by binding studies with SR4 and the tailored molecule. These identified sites and the structure of the prototype inhibitor are then used to model and identify peptides as well as small-molecule compounds also capable of interacting with the corresponding sites in the target species SR4 domain of sigma and inhibiting sigma activity. Combinatorial chemistry and other means of preparation of candidates based on the identified minimal structures needed to bind to SR4 may be carried out, using methods well known in the art.

The identified sites of interaction between *E. coli* SR4 and AsiA may be used as the starting point to prepare mutant proteins related to AsiA with altered and preferably improved binding properties to SR4, which may be used to inhibit bacterial gene transcription or preferably serve as the basis for the modeling and design of small-molecule antibiotic agents. In particular, portions of helices H1 and H3 of AsiA comprise sites of interactions with SR4 and are sites for modification to increase affinity. Among these sites of interaction, about the first 40 amino acid residues, and more particularly, amino acids 3–20 and 33–44 of AsiA have been identified as sites of interaction between AsiA and SR4, and are thus preferred amino acid residue targets for modification in order to prepare a SR4 antagonist capable of disrupting bacterial gene expression. Even more particularly, Asp 6, Glu 10, Ile 11, Ile 12, Thr 13, Leu 18, Ala 35, Phe 36, Glu 39 and Ile 40 of AsiA are site of interaction with residues Leu 559, Val 582, Ile 587, Ile 590, Leu 595, Arg 596 of SR4. Thus, these sites in AsiA are to be taken into account in the design of SR4 antagonists of other bacterial species or for increasing the antagonistic activity of AsiA. The target sites in SR4 are invariant among all eubacterial species.

A screen for evaluating the ability of compounds to antagonize sigma activity and in particular bind to the SR4 domain of sigma may be carried out in accordance with the teaching herein. In one assay, the ability of an agent to compete with the binding between a fragment of AsiA comprising about the first 40 amino acid residues of AsiA, or more particularly, amino acids 3–20 and 33–44 of AsiA, or even more particularly, 20 and 33–44 of AsiA, or even more particularly any one or a combination of Asp 6, Glu 10, Ile 11, Ile 12, Thr 13, Leu 18, Ala 35, Phe 36, Glu 39 and Ile 40 of AsiA are sites of interaction between AsiA and SR4 are used.

In one embodiment of the invention, the three-dimensional structural information of the bacteriophage T4 AsiA protein, its naturally occurring dimers, and the interface between the SR4 domain of $E\sigma^{70}$ and AsiA protein in an SR4/AsiA heterodimer is used as a target in a virtual ligand screening procedure that seeks to identify, via computer docking methods, candidate compounds from a vast compound library which bind with high affinity to the target site.

In another embodiment, the structural information of the SR4 domain is used to design compounds predicted to bind to the SR4 site, and such compounds are tested for high affinity binding. Any compounds which showed efficacy in the biological assays are then examined by NMR 'footprinting' to verify binding at the SR4 domain.

In a further embodiment of the invention, candidate compounds able to bind to the SR4 site are modified by methods known in the art to further improve specific characteristics, e.g., to increase efficacy and/or specificity and/or solubility. Selected compounds exhibiting the most desired characteristics are designated lead compounds, and further tested in, for example, mouse models to measure their efficacy as antimicrobial agents.

Virtual Ligand Screening Via Flexible Docking Technology

Current docking and screening methodologies can select small sets of likely lead candidate ligands from large libraries of compounds using a specific protein structure. Such methods are described, for example, in Abagyan and Totrov (2001) Current Opinion Chemical Biology 5:375–382, herein specifically incorporated by reference in its entirety.

Virtual ligand screening (VLS) based on high-throughput flexible docking is useful for designing and identifying compounds able to bind to a specific protein structure. VLS can be used to virtually sample a large number of chemical molecules without synthesizing and experimentally testing each one. Generally, the methods start with protein modeling which uses a selected protein structure derived by conventional means, e.g., X-ray crystallography, NMR, homology modeling. A set of compounds and/or molecular fragments are then docked into the selected binding site using any one of the existing docking programs, such as for example, MCDOCK (Liu et al. (1999) J. Comput. Aided Mol. Des. 13:435–451), SEED (Majeux et al. (1999) Proteins 37:88–105; DARWIN (Taylor et al. (2000) Proteins 41:173–191; MM (David et al. (2001) J. Comput. Aided Mol. Des. 15:157–171. Compounds are scored as ligands, and a list of candidate compounds predicted to possess the highest binding affinities generated for further in vitro and in vivo testing and/or chemical modification.

In one approach of VLS, molecules are "built" into a selected binding pocket prior to chemical generation. A large number of programs are designed to "grow" ligands atom-by-atom [see, for example, GENSTAR (Pearlman et al. L (1993) J. Comput. Chem. 14:1184), LEGEND (Nishibata et al. (1993) J. Med. Chem. 36:2921–2928), MCDNLG (Rotstein et al. (1993) J. Comput-Aided Mol. Des. 7:23–43), CONCEPTS (Gehlhaar et al. (1995) J. Med. Chem 38:466–472] or fragment-by-fragment [see, for example, GROUPBUILD (Rotsein et al. (1993) J. Med. Chem. 36:1700–1710), SPROUT (Gillet et al. (1993) J. Comput. Aided Mol. Des. 7:127–153), LUDI (Bohm (1992) J. Comput. Aided Mol. Des. 6:61–78), BUILDER (Roe (1995) J. Comput. Aided Mol. Des. 9:269–282), and SMOG (DeWitte et al. (1996) J. Am. Chem. Soc. 118:11733–11744].

Methods for scoring ligands for a particular protein are known which allow discrimination between the small number of molecules able to bind the protein structure and the large number of non-binders. See, for example, Agagyan et al. (2001) supra, for a report on the growing number of successful ligands identified via virtual ligand docking and screening methodologies.

The invention provides methods for identifying agents (e.g., candidate compounds or test compounds) that bind with high affinity to the SR4 interaction site. Agents identified by the screening method of the invention are useful as candidate anti-microbial therapeutics. For example, a method of screening for SR4 antagonists may include:

(a) contacting a test molecule with the SR4 domain of $E\sigma^{70}$, or with an SR4 fragment, and (b) determining whether the test molecule binds the SR4 domain or the SR4 fragment, wherein the test molecule binding the SR4 domain or the SR4 fragment is capable of inhibiting microbial growth.

Examples of agents, candidate compounds or test compounds include, but are not limited to, nucleic acids (e.g., DNA and RNA), carbohydrates, lipids, proteins, peptides, peptidomimetics, small molecules and other drugs. Agents can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) Anticancer Drug Des. 12:145; U.S. Pat. No. 5,738,996; and U.S. Pat. No. 5,807,683, each of which is incorporated herein in its entirety by reference).

Examples of methods for the synthesis of molecular libraries can be found in the art, for example in: DeWitt et al. (1993) Proc. Natl. Acad. Sci. USA 90:6909; Erb et al. (1994) Proc. Natl. Acad. Sci. USA 91:11422; Zuckermann et al. (1994) J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233, each of which is incorporated herein in its entirety by reference.

Libraries of compounds may be presented, e.g., presented in solution (e.g., Houghten (1992) Bio/Techniques 13:412–421), or on beads (Lam (1991) Nature 354:82–84), chips (Fodor (1993) Nature 364:555–556), bacteria (U.S. Pat. No. 5,223,409), spores (U.S. Pat. Nos. 5,571,698; 5,403,484; and 5,223,409), plasmids (Cull et al. (1992) Proc.

Natl. Acad. Sci. USA 89:1865–1869) or phage (Scott and Smith (19900 Science 249:386–390; Devlin (1990) Science 249:404–406; Cwirla et al. (1990) Proc. Natl. Acad. Sci. USA 87:6378–6382; and Felici (1991) J. Mol. Biol. 222: 301–310), each of which is incorporated herein in its entirety by reference.

Screening Assays

Small molecules identified through the above described virtual ligand docking and screening methodologies are further tested in in vitro and in vivo assays.

In one embodiment, agents that interact with (i.e., bind to) the SR4 site are identified in a cell-based assay system. In accordance with this embodiment, cells expressing a protein or a fragment thereof containing the SR4 site, are contacted with a candidate compound or a control compound and the ability of the candidate compound to interact with the SR4 is determined. If desired, this assay may be used to screen a plurality (e.g. a library) of candidate compounds. The cell, for example, can be of prokaryotic origin (e.g., E. coli) or eukaryotic origin (e.g., yeast or mammalian). Further, the cells can express the SR4, or SR4 fragment, endogenously or be genetically engineered to express the SR4, or SR4 fragment. In certain instances, the SR4 or SR4 fragment is labeled, for example with a radioactive label (such as $^{32}$P, $^{35}$S or $^{125}$I) or a fluorescent label (such as fluorescein isothiocyanate, rhodamine, phycoerythrin, phycocyanin, allophycocyanin, o-phthaldehyde or fluorescamine) to enable detection of an interaction between the SR4 and a candidate compound. The ability of the candidate compound to bind to the SR4 site can be determined by methods known to those of skill in the art. For example, the interaction between a candidate compound and the SR4 site can be determined by flow cytometry, a scintillation assay, immunoprecipitation or western blot analysis.

In another embodiment, agents that interact with (i.e., bind to) the SR4 domain of E$\sigma^{70}$, or a relevant fragment thereof, are identified in a cell-free assay system. In accordance with this embodiment, a native or recombinant SR4 or fragment thereof is contacted with a candidate compound or a control compound and the ability of the candidate compound to interact with the SR4 domain of E$\sigma^{70}$ is determined. If desired, this assay may be used to screen a plurality (e.g. a library) of candidate compounds. In one embodiment, the SR4 or fragment thereof is first immobilized, by, for example, contacting with, for example, an immobilized antibody which specifically recognizes and binds it, or by contacting a purified preparation of the SR4 or fragment thereof, with a surface designed to bind proteins. The SR4 domain or E$\sigma^{70}$ site-containing SR4 fragments may be partially or completely purified (e.g., partially or completely free of other polypeptides) or part of a cell lysate. Further, the SR4 or E$\sigma^{70}$ site containing SR4 fragments may be a fusion protein comprising the SR4 site or a biologically active portion thereof. Alternatively, the SR4 or E$\sigma^{70}$ site containing SR4 fragments thereof can be biotinylated using techniques well known to those of skill in the art (e.g., biotinylation kit, Pierce Chemicals; Rockford, Ill.). The ability of the candidate compound to interact with the SR4 site can be determined by methods known to those of skill in the art. The detailed interaction between the candidate compound or a library of compounds can be analyzed with amino-acid resolution by examination of $^{15}$N and/or $^{13}$C enriched SR4 and looking for specific changes in chemical shifts in the presence of the candidate compounds employing a method described herein as NMR 'footprinting'.

In another embodiment, agents that modulate the activity of SR4 (decrease or lessen) are identified in an animal model. Examples of suitable animals include, but are not limited to, mice, rats, rabbits, monkeys, guinea pigs, dogs and cats. Preferably, the animal used represents a model of microbial infection. In accordance with this embodiment, the test compound or a control compound is administered (e.g., orally, rectally or parenterally such as intraperitoneally or intravenously) to a suitable animal and the effect on the background level of SR4 activity is determined.

EXAMPLES

Experimental Procedures

Preparation of Proteins: AsiA cDNA was inserted in pET3a and the protein expressed in modified BL21(DE3) cells in which the T7 RNAP gene was under the control of a salt inducible promoter. Modified BL21(DE3) cells were grown by adaptive control fermentation (Werner et al., 2001, Methods Enzymol. 338: 283–305) employing $^{15}$NH$_4$Cl and/or $^{13}$C-glucose and induced for 2 hrs by addition NaCl and IPTG to a final concentration of 150 mM and 0.4 mM, respectively. The protein was extracted by French press and purified by a combination of anion-exchange (Q-sepharose) and gel-filtration (Sephacryl S-100HR) chromatographies in pH 8 Tris-HCl. Purity and homogeneity of the protein product were determined by SDS-PAGE and MALDI mass spectrometry. A cDNA encoding either residues 533–609 ($\sigma$533) or 537–609 ($\sigma$537) of E. coli $\sigma^{70}$ was inserted into pET30b and expressed in HMS174(DE3) cells in the presence of 0.5 mM IPTG for 2 hours. The two $\sigma^{70}$ constructs were used interchangeably without functional distinction. These constructs removed a C-terminal Phe residue which reduced the solubility of the AsiA/$\sigma$537 or AsiA/$\sigma$533 complex without altering the binding properties for AsiA (Severinov and Muir, 1998, J. Biol. Chem. 273: 16205–16209). The sigma proteins were purified from inclusion bodies by a combination of cation-exchange (SP-sepharose) chromatography in the presence of 50 mM Tris-HCl, 4 M urea at pH 7.5 followed by cation-exchange (Source 15S) chromatography under non-denaturing conditions.

The dimer interface was analyzed by asymmetrical labeling in which $^{13}$C/$^{15}$N-labeled and unlabeled AsiA were denatured and mixed in a ratio of 1:1.05 to create a sample in which only one monomer was $^{13}$C-enriched. The extent of labeling was determined by integration of an isolated methyl-group resonance in one-dimensional NMR spectra in which the $^1J_{CH}$ coupling was either active or suppressed by broadband $^{13}$C decoupling during acquisition.

Complexes of AsiA and $\sigma$537 or $\sigma$533 for NMR studies were prepared in two ways with identical results. First, denatured $\sigma$537 or $\sigma$533 was rapidly diluted into a solution of AsiA in 10 mM sodium phosphate, 50 mM NaCl, pH 6.2 to a final guanidine HCl (GnHCl) concentration of 0.1 M followed by dialysis to remove the residual GnHCl. Second, complexes were prepared by placing both AsiA and $\sigma$537 or $\sigma$533 in 6 M GnHCl in phosphate buffer followed by gradual removal of the GnHCl by dialysis. Complexes of AsiA and $\sigma$537 for crosslinking studies were prepared by first removing denaturant from stock solutions of $\sigma$537 (0.6 mg/ml) and subsequently adding a stoichiometric quantity of AsiA. Complexes of AsiA and $\sigma$533 for mass spectrometry studies were similarly prepared without the aid of denaturant. In all cases, the protein complex solutions were concentrated by centrifugal ultrafiltration.

Analytical Ultracentrifugation. All sedimentation velocity and equilibrium experiments were performed with a Beckman Optima XL-I. Velocity, equilibrium and Monte Carlo analyses were performed with UltraScan version 5.0 (Demeler, 2001). Hydrodynamic corrections for buffer conditions were made according to data published by Laue et al. (*Analytical Ultracentrifugation in Biochemistry and Polymer Science*, pp. 90–125, 1992), and as implemented in UltraScan. The partial specific volume of AsiA was estimated according to the method by Cohn and Edsall (*Proteins, Amino acids and Peptides as Ions and Dipolar Ions*, 1943), and as implemented in UltraScan. Monte Carlo analyses were calculated on a 40 processor Linux Beowulf cluster running Slackware Linux version 7.0. All samples were analyzed in a buffer containing 10 mM sodium phosphate, pH 6.2, with 10 mM NaCl. Sedimentation velocity experiments were performed at 60,000 rpm and 20° C. The samples were spun with double sector aluminum centerpieces in the AN-60-TI rotor. Scans were collected at either 230 nm or 280 nm in continuous radial mode with 0.001 cm steps and no averaging. Sedimentation equilibrium experiments were performed at 20° C. and speeds ranging between 15,000–50,000 rpm. Samples were spun in double sector epon/charcoal centerpieces in the AN-50-TI rotor. Scans were collected at equilibrium at either 230 or 280 nm in radial step mode with 0.001 cm steps and 50 point averaging. Multiple loading concentrations ranging between 0.2–0.7 OD were measured at the given wavelength, data exceeding 0.9 OD were excluded from the fit.

NMR spectroscopy. Samples of $^{13}C$ and/or $^{15}N$-enriched AsiA were concentrated to 1 mM in 10 mM sodium phosphate, 50 mM NaCl, 1 mM benzamidine HCl, pH 6.2 and assignments conducted at 25° C. using standard techniques on Bruker DMX 500 and DMX 600 spectrometers. $^{3}J_{NH\alpha}$, $^{3}J_{NH\beta}$, $^{3}J_{C\gamma N}$, $^{3}J_{C\gamma CO}$ coupling constants were measured by quantitative J correlation spectroscopy (Vuister et al., *Biological Magnetic Resonance* 16, pp. 195–259, 1999). $^{15}N$-edited and $^{13}C$-edited three and four dimensional NOE spectroscopy was conducted with mixing times of 110 ms ($^{15}N$) and 100 ms ($^{13}C$), respectively. Secondary structure elements were identified from a combination of secondary $^{13}C_{\alpha}$ and $^{13}C_{\beta}$ shifts using the chemical shift index (Wishart et al., 1992, Biochemistry 31: 1647–1651) as well as the pattern and intensity of NOEs observed in $^{15}N$-edited NOESY (Wüthrich, 1986, *NMR of Proteins and Nucleic Acids*). The dimer interface was identified by $^{13}C-F_1$-filtered/$F_3$-edited NOESY (Zwahlen et al., 1999, J. Am. Chem. Soc. 119: 6711–6721) and $^{13}C$-edited NOESY using an asymmetrically labeled sample as described. The changes in N and $H_N$ chemical shifts which defined the 'footprint' were calculated according to the following equation: $\Delta ppm = [(N_{bound} - N_{free})^2 + (H_{N\,bound} - H_{N\,free})^2]^{1/2}$ (Nagata et al., 2001, J. Mol. Biol. 308: 191–203).

Crosslinking. Purified AsiA or AsiA/σ537 complexes were examined for homogeneity on non-denaturing 20% Tris-alanine PAGE (pH 8.8) at a concentration of 0.5–0.6 mg/ml in pH 6.2 sodium phosphate, 50 mM NaCl. 15 µg of protein or protein complex were mixed with disuccinimidyl glutarate (DSG) at a final [DSG]=67 µM and reacted for 30 minutes on ice in a final volume of 21 µl. The reaction was quenched with 1 µl 3 M Tris-HCl (pH 8) for 15 minutes followed by the addition of SDS loading dye. The crosslinked species were analyzed on 16% Tris-tricine gels.

Pulldown assay with crosslinked AsiA. Purified AsiA (0.5 mg/ml) was crosslinked with 10 µl 2 mM DSG in DMSO and incubated 30 min at room temperature. The reaction was quenched with 5 µl 0.3M Tris-HCl pH 8.0 buffer. The pulldown assay was performed by cloning σ537 into pET15b (Novagen) with an N-terminal His$_6$ affinity tag and immobilizing the expressed protein on Ni$^{2+}$-sepharose using standard procedures. The σ537-loaded beads (20 µl) were then incubated with either AsiA or pre-crosslinked AsiA in 150 µl of a binding buffer containing 10 mM sodium phosphate, 150 mM NaCl, 0.2% NP-40 (w/v), 5% glycerol (w/v), 1 mM benzamidine HCl, 50 mM imidazole. After 2 hrs incubation at 4° C., the beads were pelleted, washed twice with 200 µl binding buffer, eluted with SDS-PAGE loading dye and visualized by coomassie blue staining following 16% Tris-tricine PAGE. Control reactions were performed identically using Ni$^{2+}$-sepharose beads lacking σ537.

Mass spectrometry: AsiA, σ533 enriched with $^{15}N$ and a mixture of an AsiA/σ533 complex with AsiA homodimer were analyzed using sinapinic acid (Sigma) as a matrix. Solvent conditions were optimized to prevent disruption of labile contacts (Cohen et al., 2000, Anal. Chem. 72: 574–579). Sinapinic acid matrix was prepared as a saturated solution in a 2:1 (v/v) mixture of water and acetonitrile. Samples at a concentration of 0.6 to 3.4 mg/ml were diluted 1:10 to 1:30 in matrix solution. Apomyoglobin (Sigma) was at 400 nM was used as an internal mass calibrant. A small aliquot (0.5 µl) of protein-matrix solution was spotted onto the sample plate using an ultra-thin layer method (Cadene and Chait, 2000, Anal. Chem. 72: 5655–5658).

All mass measurements were performed on a Voyager DE-STR (Perseptive Biosystems, Foster City, Calif.) MALDI-TOF MS, operating in positive linear, delayed extraction mode. This instrument is equipped with a nitrogen laser delivering pulses of ultraviolet light (wavelength 337 nm) at 3.5 Hz to the matrix spot. Spectra from 200 individual laser shots were averaged (using a 1 ns data channel width) with software provided by the manufacturer. The spectra were calibrated externally and internally and further analyzed using the program M-over-Z (http://www.proteometrics.com, http://prowl.rockefeller.edu).

Mutagenesis: Site-specific mutants of AsiA were introduced using the Stratagene 'Quick-change' kit according to the manufacturer's instructions. The mutant plasmids were transformed into salt-inducible BL21(DE3) cells and expressed as described above. Crude lysate containing the expressed AsiA protein was prepared by sonication in 10 mM sodium phosphate, pH 6.2, 150 mM NaCl, 10 mM benzamidine HCl, 20 µg/ml PMSF, 0.25% NP-40, 5% glycerol. 1 ml of crude lysate was then mixed with 100 µl of His$_6$-σ537 immobilized on Chelating Sepharose Fast Flow (Amersham/Pharmacia). The binding reaction was carried out at 4° for 3 hours followed by 2×1 ml washes of the sepharose beads in the same buffer. The proteins were eluted from the beads with SDS-PAGE loading dye and visualized by coomassie blue staining.

Structure determination. NOEs within the protein were grouped into four distance ranges as previously described (Omichinski et al., 1997, Nat. Struct. Biol. 4:122–132). Distances involving methyl groups, aromatic ring protons and non-stereospecifically assigned methylene protons were represented as a $(\Sigma^{-6})^{-1/6}$ sum. φ, $\chi_1$ and $\chi_2$ angles were derived from $^3J$ coupling constants and qualitative analysis of heteronuclear NOEs as previously described (Vuister et al., 1999, *Biological Magnetic Resonance* 16, pp. 195–259). Protein backbone hydrogen bonding restraints ($r_{NH-O}$=1.5–2.8 Å, $r_{N-O}$=2.4–3.5 Å) within areas of regular secondary structure were introduced during the final stages of refinement. The minimum ranges employed for φ, $\chi_1$ and $\chi_2$ torsion angle restraints were ±30°. The structures were calculated with the program XPLOR-3.843 (Brünger, 1992, Cell 58: 1163–1171) adapted to incorporate pseudo-potentials for $^3J_{NH\alpha}$ coupling constants (Garrett et al., 1994), $C_\alpha$ and $C_\beta$ chemical shifts (Kuszewski et al., 1995, J. Magn. Reson. 106: 92–96) and a conformational database potential (Kuszewski et al., 1997, J. Magn. Reson. 125: 171–177) employing a hybrid protocol as previously described (O'Donoghue et al., 1996, J. Biomol. NMR 8: 193–206; Omichinski et al., 1997, Nat. Struct Biol. 4:122–132). There were no hydrogen-bonding, electrostatic or 6–12 Lennard-Jones empirical potential energy terms in the target function. Structure quality was assessed with PROCHECK_NMR (Laskowski et al., 1996, J. Biol. NMR 8: 477–486) and Prosa II (Sippl 1993) (Table 1).

Results

AsiA is dimeric in solution. During purification of recombinant AsiA from E. coli, it was observed that AsiA eluted from gel filtration chromatography at approximately twice its molecular weight, suggesting that AsiA was dimeric in solution. Analytical ultracentrifugation of the purified protein confirmed AsiA to be a dimer. van Holde-Weischet analysis (van Holde & Weischet, 1978, Biopolymers 17: 1387–1403) of sedimentation velocity experiments conducted at different concentrations (Carruthers et al., 2000, Methods Enzymol. 321:66–80) revealed a mixture of monomer and dimer at low concentration (9.8 $\mu$M) and mostly dimer at high concentration (68.4 $\mu$M). A combined integral distribution plot for the different concentration samples clearly indicates a concentration dependent, reversible association event, which results in the formation of almost exclusively dimer at the higher concentration. The integral distribution plot of S20,W for the low concentration sample displays the typical half-parabola shape of a self-association event (Demeler et al., 1997, Biophys. J. 72: 397–407) (not shown). Finite element analysis of the high concentration data resulted in random residuals and revealed a molecular weight of 19.64±0.2 kD, in good agreement with the theoretical molecular weight of an AsiA dimer (21.18 kD). The frictional coefficient of $3.58 \times 10^{-8}$ and frictional ratio, $f/f_0$, of 1.13 suggests a mostly globular conformation of the dimer.

To further establish the association properties of AsiA, sedimentation equilibrium experiments were conducted over a large concentration range and experimental data collected at multiple wavelengths (FIG. 1) (Johnson et al., 1981, Biophys. J. 36: 575–588). To analyze the data under multiple rotor speeds, wavelengths and concentrations, the monomer molecular weight and association constant were considered global parameters and forced to be the same for all included datasets (Johnson et al., 1981, Biophys. J. 36: 575–588). The wavelength scans were globally fit to a sum of Gaussian terms, whose width, amplitude and offset were allowed to float but considered global for all scans. For the global equilibrium analysis, 38 equilibrium scans from speeds ranging between 15,000 rpm and 50,000 rpm and loading concentrations between 0.2 to 0.7 optical density units (O.D.s) at both 230 nm and 280 nm were fit to both monomer-dimer and monomer-dimer-tetramer models (FIGS. 1E and 1F). Although the monomer-dimer-tetramer fit indicated the presence of small amounts of tetramer, the variance of the fit was insignificantly reduced by adding the additional parameter for the monomer-tetramer association. Thus, the system could be well described by a monomer-dimer equilibrium model, which resulted in random residuals and a monomer molecular weight of 10.36±0.077 kD (FIG. 1C), which is in excellent agreement with the molecular weight derived from the protein sequence (10.59 kD). The association constant of $1.58 \pm 0.404 \times 10^6$ M$^{-1}$ suggests fairly tight binding for the dimer (FIG. 1D).

Three-dimensional structure of AsiA. The three-dimensional structure of AsiA was determined from 1353 experimental distance restraints and 209 dihedral angle restraints per monomer employing standard techniques for chemical shift assignment and structure determination. 89$\phi$ and 55 $\chi_1$ restraints were derived from $^3J_{NH\alpha}$, $^3J_{H\alpha H\beta}$ and $^4J_{NH\beta}$ coupling constants; 65 $\Psi$ restraints were determined by chemical shift database analysis with the program TALOS (Cornilescu et al., 1999, J. Biol. NMR 13: 289–302). The 29 lowest energy structures displayed a root-mean-square coordinate deviation relative to the mean structure of 0.35 Å for backbone atoms and 0.86 Å for all non-hydrogen atoms (Table 1).

TABLE 1

STRUCTURAL STATISTICS[a]

| | <SA> |
|---|---|
| RMS deviations from exptl distance restraints per monomer (Å)[b] | |
| All (1353) | 0.058 ± 0.002 |
| sequential (\|i − j\| = 1) (350) | 0.035 ± 0.005 |
| short range (1 < \|i − j\| 5) (400) | 0.066 ± 0.003 |
| long range (\|i − j\| > 5) (230) | 0.077 ± 0.005 |
| intraresidue (283) | 0.053 ± 0.005 |
| H-bonds (90) | 0.062 ± 0.006 |
| RMS deviations from exptl distance restraints dimer (Å)[b] | |
| All (64) | 0.097 ± 0.008 |
| RMS deviations from exptl restraints per monomer | |
| dihedral (deg) (209) | 0.74 ± 0.067 |
| $^3J_{NH\alpha}$ coupling constants (Hz) (75) | 0.97 ± 0.04 |
| Deviations from idealized covalent geometry | |
| bonds (Å) | 0.0049 ± 0.0004 |
| angles (deg) | 0.64 ± 0.02 |
| impropers (deg) | 0.54 ± 0.02 |
| Coordinate precision of dimer[c] | |
| backbone (residues 2–90) | 0.35 ± 0.04 |
| all non-hydrogen atoms (residues 2–90) | 0.86 ± 0.05 |
| Quality Factors for dimer[d] | |
| % residues in most favorable Ramachandran (5162) | 84.5% |
| Prosa II Z score | −7.2 ± 0.34 |

[a]RMS deviations are calculated relative to the mean coordinates <SA> for the family of 29 simulated annealing structures excluding residue 1.
[b]No restraints between protons separated by 3 bonds were utilized.
[c]The precision of the coordinates is defined as the average atomic rms difference between the 29 individual simulated annealing structures and the mean coordinates <SA> for residues 2–90 in the dimer.
[d]PROCHECK_NMR and ProsaII were used to assess the overall quality of the structures for residues 2–90 in the dimer.

Figure 2:
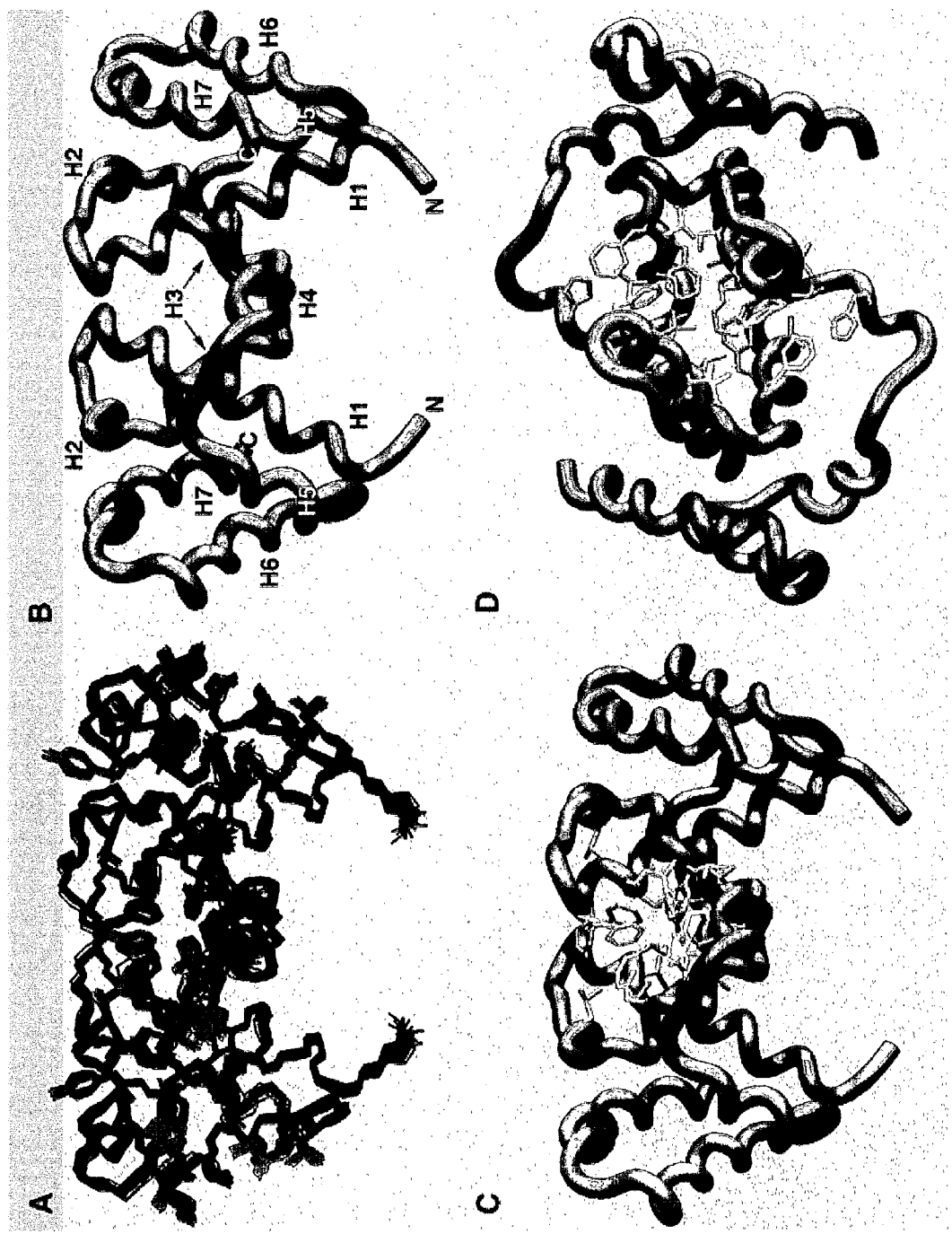
FIG. 2: Three-dimensional structure of the AsiA dimer. A) The superposition of the 29 structures is shown for the non-hydrogen backbone atoms in purple and selected side chains in red. The coordinate precision for the structure family was 0.35 Å RMSD from the mean for the backbone atoms and 0.86 Å RMSD from the mean for all non-hydrogen atoms. B) Identical view of the AsiA dimer representing the backbone of the protein as a purple worm. The relative orientation of the helices in each monomer is indicated and illustrates the overlapping helix-loop helix elements. HLH1=α-helix H1 (Asn 4-Lys 20), loop L1 (Phe 21-Thr 23) and α-helix H2 (Glu 24-Glu 28). HLH2=α-helix H3 (Arg 30-Gly 41) and $3_{10}$ helix H4 (residues Thr 43-Arg 47). HLH3=α-helix H5 (Gln 51-Ser 59), loop L2 (Glu 60-Thr 62) and α-helix H6 (Gln 63-Glu 72). HLH4=α-helix H6 (Gln 63-Glu 72) and α-helix H7 (Asn 74-Met 86). C, D) Two views of the AsiA dimer interface. In C), the view is identical to A) and B). In panel D), the view is rotated 90° about the horizontal axis. Non-polar amino acids are shown in yellow (Thr 13, Val 14, Ile 17, Leu 18 and Phe 21 of helix H1, Phe 33, Phe 36, Leu 37 and Ile 40 of helix H3 and His 44), positively charged amino acids in pale blue (Lys 20). The view in D) is rotated 90° about the horizontal axis relative to the view shown in A–C).

AsiA is an unusual seven-helix bundle composed of overlapping helix-loop-helix elements (HLH) (FIGS. 2A and 2B). Within each HLH element, the helical axes are oriented antiparallel to one another. The first and last HLH elements are oriented in approximately parallel planes with the paired helix axes of the two HLH elements orthogonal to one another. Six of the seven helices are amphipathic, with helix H1 displaying an alternation of polar and non-polar surfaces. This alternation is required to form the hydrophobic core of the monomer in the first half of helix H1 (residues 4–12) and required to form the hydrophobic dimer interface in the second half of helix H1 (residues 13–20). Helix H3 is entirely hydrophobic, forming the hydrophobic interior of each monomer and the dimer interface.

Approximately 1,854 Å² of accessible surface are buried at the dimer interface. The interface is almost entirely hydrophobic, composed of residues principally located in helices H1 and H3 (FIGS. 2B and 2C). Thr 13, Val 14, Ile 17, Leu 18, Lys 20 and Phe 21 of helix H1 in one monomer contact Glu 24, Phe 33, Phe 36, Leu 37 and Ile 40 of helix H3 in the second monomer. At the top and bottom of the interface, charged residues are inferred to form salt bridges to cap the hydrophobic interior.

Figure 3:
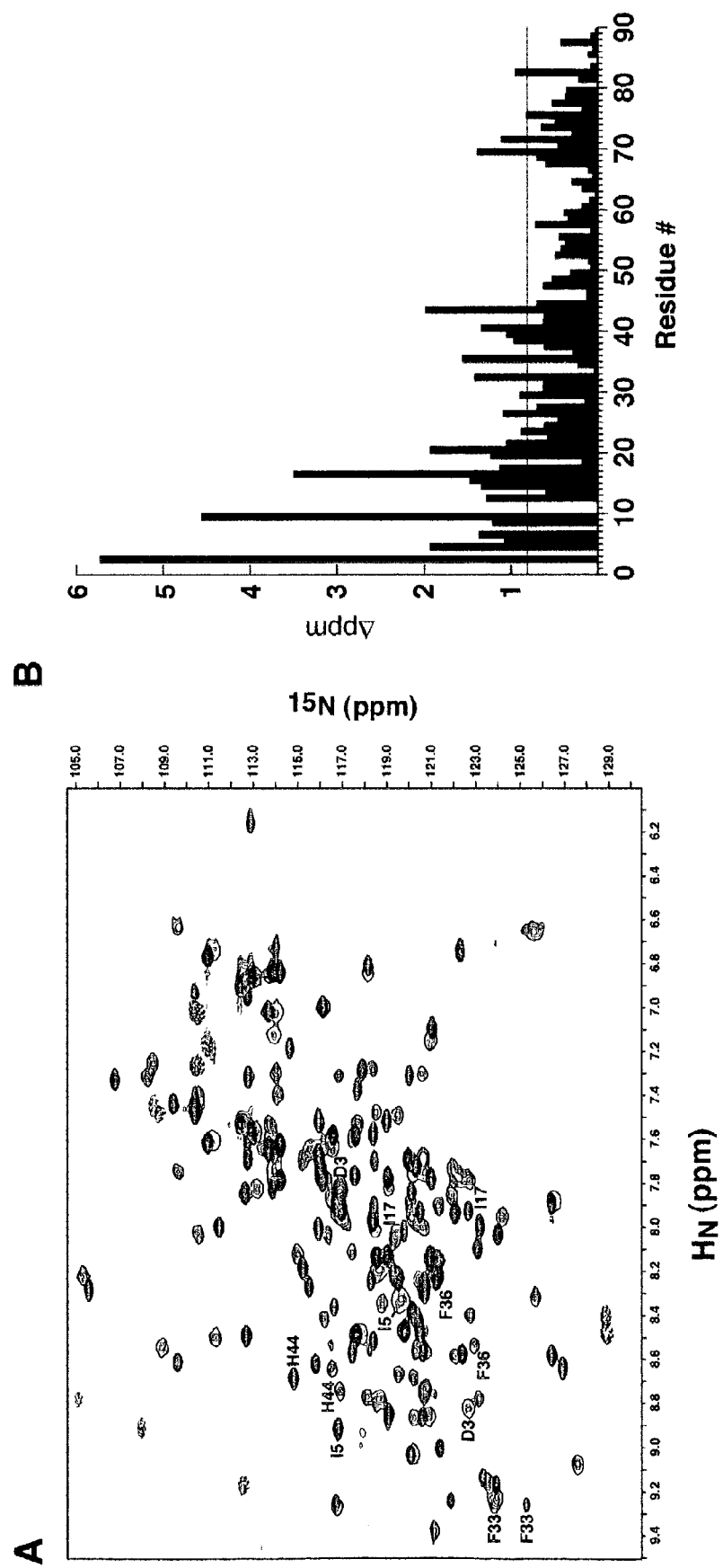
FIG. 3: Analysis of the σ537 binding surface by NMR 'footprinting'. A) AsiA homodimer (black) and the AsiA/σ537 heterodimer (red) were analyzed by $^{15}N$-$^1H$ HSQC spectroscopy with $^{15}N$-labeled AsiA and unlabeled σ537. The positions of several residues which move substantially upon addition of σ537 are shown in black for the AsiA homodimer and in red for the AsiA/σ537 complex. B) A histogram of the composite chemical shift changes (see Materials and Methods) define a broad 'footprint' (>0.8 ppm change) of σ537 on AsiA which encompasses many of residues 3–20 and residues 33, 36, 39–40 and 44. These residues reside along the homodimer interface of AsiA.

Coincidence of the AsiA homo- and heterodimer interfaces. NMR 'footprinting' of AsiA bound to SR4 (σ537, residues 537–609, see Materials and Methods) enabled identification of a local surface of AsiA which was perturbed upon formation of an AsiA/SR4 complex. Analysis of the combined backbone N and $H_N$ chemical shift differences between spectra of AsiA homodimer and the AsiA/SR4 complex defined a broad 'footprint' encompassing many of residues 3–20 and residues 33–44 (FIG. 3). These regions are located within helices H1, H3, H4 and in the irregular loop between helices H4 and H5, i.e. the segments of the monomer which form the homodimer interface. This suggests that either the homodimer interface is altered upon binding SR4 or that the SR4 binding surface is at least partially overlapping with the homodimer interface.

Figure 4:
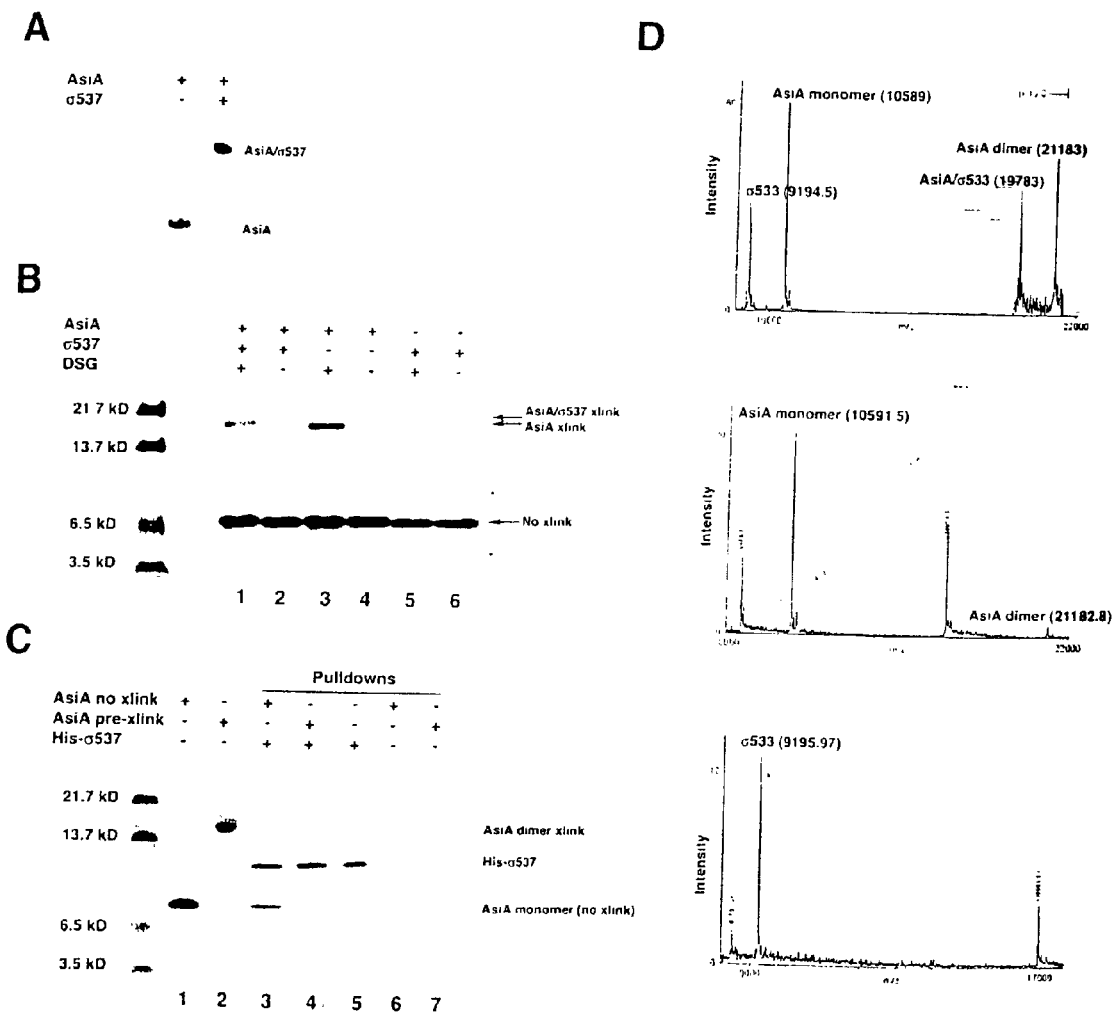
FIG. 4: AsiA forms a 1:1 complex with SR4. A) Non-denaturing Tris-alanine PhastGel (Amersham/Pharmacia) at pH 8.8 demonstrating the homogeneity of the AsiA homodimer and AsiA/σ537 complex preparations used for protein crosslinking with disuccinimidyl glutarate (DSG). σ537 fails to run into this gel matrix. B) Denaturing SDS-Tricine PAGE of homodimers and AsiA/σ537 complexes following crosslinking with DSG. σ537 fails to form a crosslink with DSG (lanes 5 and 6), in contrast to the AsiA homodimer (lanes 3 and 4) and the AsiA/σ537 complex (lanes 1 and 2). Crosslinking with the AsiA homodimer produces a major and minor species (lane 3), while crosslinking the heterodimer produces a single species of slightly different mobility with apparently the same size as the crosslinked AsiA homodimer. Note that non-denaturing PAGE (a) establishes that the crosslinked species in each case are either pure homodimer (lane 3) or pure complex (lane 1). C) Pre-crosslinked AsiA does not bind σ537 in a affinity tag pulldown experiment. Solutions of purified AsiA (lane 1) or purified AsiA crosslinked with DSG (lane 2) were probed with N-terminal His$_6$-tagged σ537 immobilized on Ni$^{2+}$-sepharose. While uncrosslinked AsiA was pulled down by His-σ537 (lane 3), pre-crosslinked AsiA was no longer capable of binding His-σ537 (lane 4). This indicates that an AsiA dimer which cannot dissociate is unable to bind σ537 in solution. Lanes 6 and 7 indicate that neither uncrosslinked AsiA (lane 6) nor pre-crosslinked AsiA (lane 7) bind to Ni$^{2+}$-sepharose on its own. D) MALDI of AsiA, σ533 and AsiA/σ533 complexes (see Materials and Methods for details). The mass spectrum of the AsiA homodimer and σ533 are shown alone in the middle and bottom panels, respectively. The peaks bracketing the main peak are those of the myoglobin calibrant with the +1 ion at 16951.5 and the +2 ion at 8475.75. The top panel shows the mass spectrum of the AsiA/σ533 mixture with AsiA homodimer. In this spectrum, the masses of both protein complexes are seen, along with each of the monomer species from which they are derived. This demonstrates that the mass of the AsiA/σ533 complex is that of a 1:1 complex with complete subunit dissociation from homodimer to heterodimer.

The relative size of the AsiA homodimer and the AsiA/SR4 complex was established by protein crosslinking and mass spectrometry. Crosslinking with disuccinimidyl glutarate (DSG) occurs between primary amines situated within 7.7 Å of one another, therefore DSG is capable of crosslinking both the AsiA homodimer and its complex with SR4 since lysine and arginine residues are present in the vicinity of both the homodimer interface (Lys 9, Lys 20, Lys 30 in AsiA) and the presumptive AsiA binding surface of SR4 (Lys 593, Arg 596 in SR4; Minakhin et al., 2001). Analysis of the size of the crosslinked species formed with free AsiA revealed that the crosslinked protein was of a size consistent with a homodimer (FIG. 4B, lanes 3–4). This was in agreement with sedimentation equilibrium data (FIG. 1), suggesting that crosslinking with DSG could probe the stoichiometry of AsiA protein complexes. Quite unexpectedly, the apparent size of the crosslinked species formed from the AsiA/SR4 complex was essentially the same as crosslinked AsiA alone (FIG. 4B, lanes 1–2). SR4 itself fails to form crosslinks with DSG (FIG. 4B, lanes 5–6). Gel filtration of the NMR sample of AsiA/SR4 (not shown) also revealed that the AsiA homodimer and the AsiA/SR4 complex were of comparable size. This indicates that the AsiA homodimer is most likely disrupted upon binding SR4 to form the AsiA/SR4 complex.

Crosslinking and gel filtration of the AsiA/σ537 complex suggested that the AsiA homodimer completely dissociated to form the AsiA/σ537 complex. Thus, an undissociable form of AsiA would be expected to be unable to bind σ537. This indeed is the case as demonstrated in FIG. 4C. A covalently crosslinked AsiA dimer is unable to associate with σ537 in a $His_6$-tag affinity pulldown experiment (FIG. 4C, lanes 2 and 4). By contrast, uncrosslinked AsiA retains the ability to bind σ537 in this assay system (FIG. 4C, lanes 1 and 3). In conjunction with NMR footprinting, crosslinking of the AsiA/σ537 complex and gel filtration, the data support the notion that the AsiA homodimer must dissociate to permit σ537 to bind.

Stoichiometry of the AsiA/SR4 complex. The stoichiometry of the AsiA/SR4 complex was established by matrix-assisted laser desorption ionization mass spectrometry (MALDI). Mass analysis conducted on AsiA, SR4 (σ533, residues 533–609) and on mixture of AsiA/σ533 complex and AsiA homodimer. FIG. 4D demonstrates that the individual masses of the AsiA homodimer and AsiA/σ533 complex (21,183 kD and 19783 kD, respectively) are equal to the expected sum of the measured masses of the AsiA monomer (measured 10591.5±3 kD, theoretical 10590.5 kD) with itself or the expected sum of AsiA monomer plus σ533 (measured 9196.0±3 kD, theoretical 9196 kD). Thus, the AsiA/σ533 complex is formed by complete dissociation of the AsiA dimer, resulting in a 1:1 heterodimeric complex.

Figure 5:
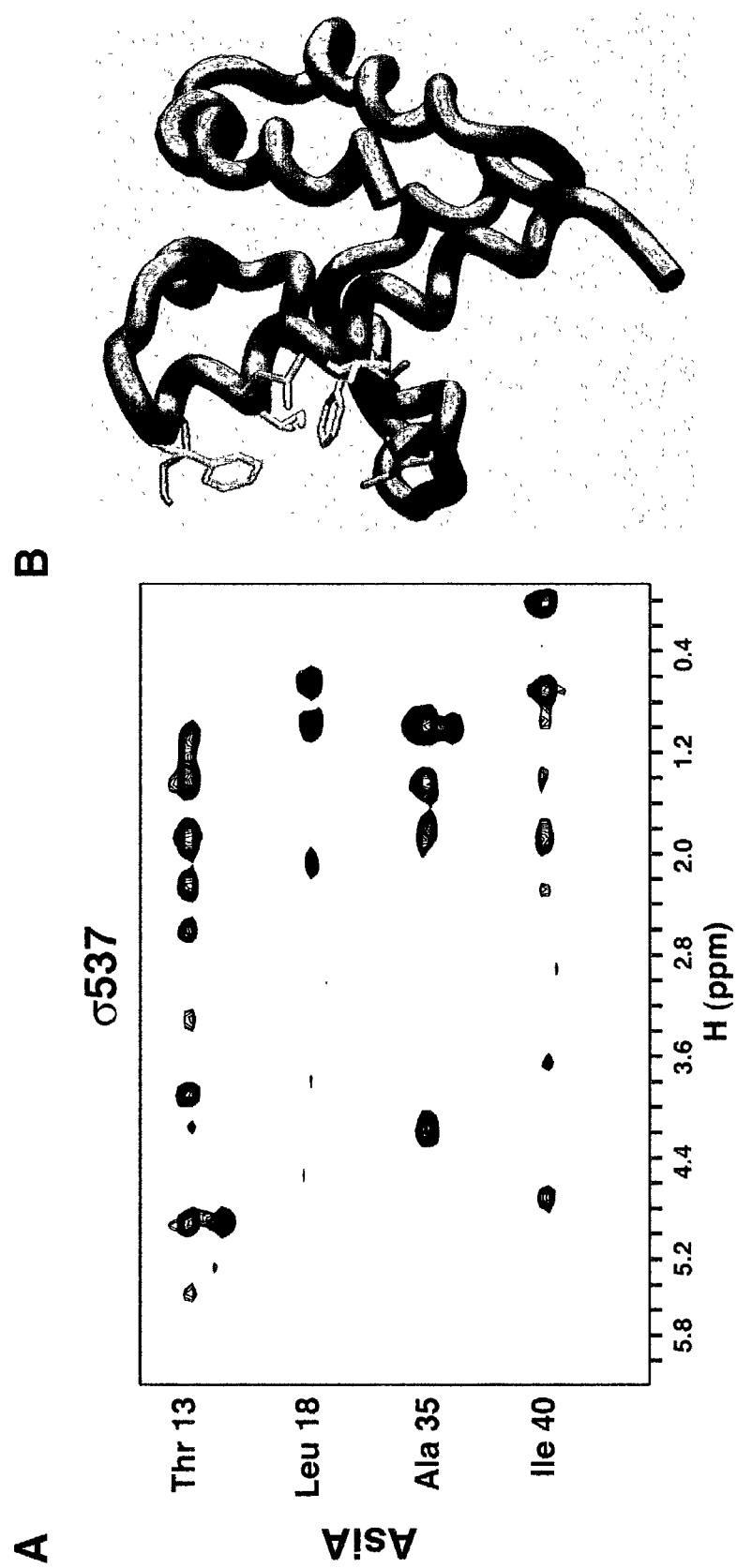
FIG. 5: The homodimer and heterodimer interfaces of AsiA are coincident. A) The AsiA/σ537 complex was asymmetrically labeled with $^{13}$C/$^{15}$N incorporation into AsiA and no labeling in σ537. A partial map of the AsiA/σ537 interface was visualized by F1-filtered/F3-edited $^{13}$C-NOESY (Zwahlen et al, 1999) and AsiA residues at the interface assigned by standard techniques. B) The identified residues at the AsiA/σ537 interface are mapped onto the AsiA monomer, which represents the right monomer in FIG. 2C. Residues at the homodimer interface are shown in yellow and purple as described in FIG. 2C; residues which participate in both the homo- and heterodimer interfaces are shown in red. Ala 35 is obscured in this view and cannot be seen.

Characterization of the SR4 binding surface of AsiA. Interfacial NOEs were observed between AsiA and SR4 and assigned to specific residues in the AsiA sequence to further characterize the SR4 binding surface of AsiA. These residues are found only at the homodimer interface, reinforcing the notion of complete subunit exchange from homodimer to heterodimer. FIG. 5 displays a partial map of the AsiA residues which form direct contacts with SR4. These residues, Thr 13, Leu 18, Ala 35, Ile 40, clearly encompass the surface of the AsiA monomer which forms the homodimer interface (compare FIGS. 2C and 2D with FIG. 5B). Complete analysis of the NMR spectrum of the AsiA/SR4 complex reveals an interaction map for the non-polar amino-acids of AsiA in which residues Ile 11, Ile 12, Thr 13, Leu 18, Ala 35 and Ile 40 interact with residues Leu 559, Val 582, Ile 587, Ile 590 and Leu 595 of SR4. Additional charged amino acids are also present at this interface, as defined by site-directed mutagenesis described below.

Figure 6:
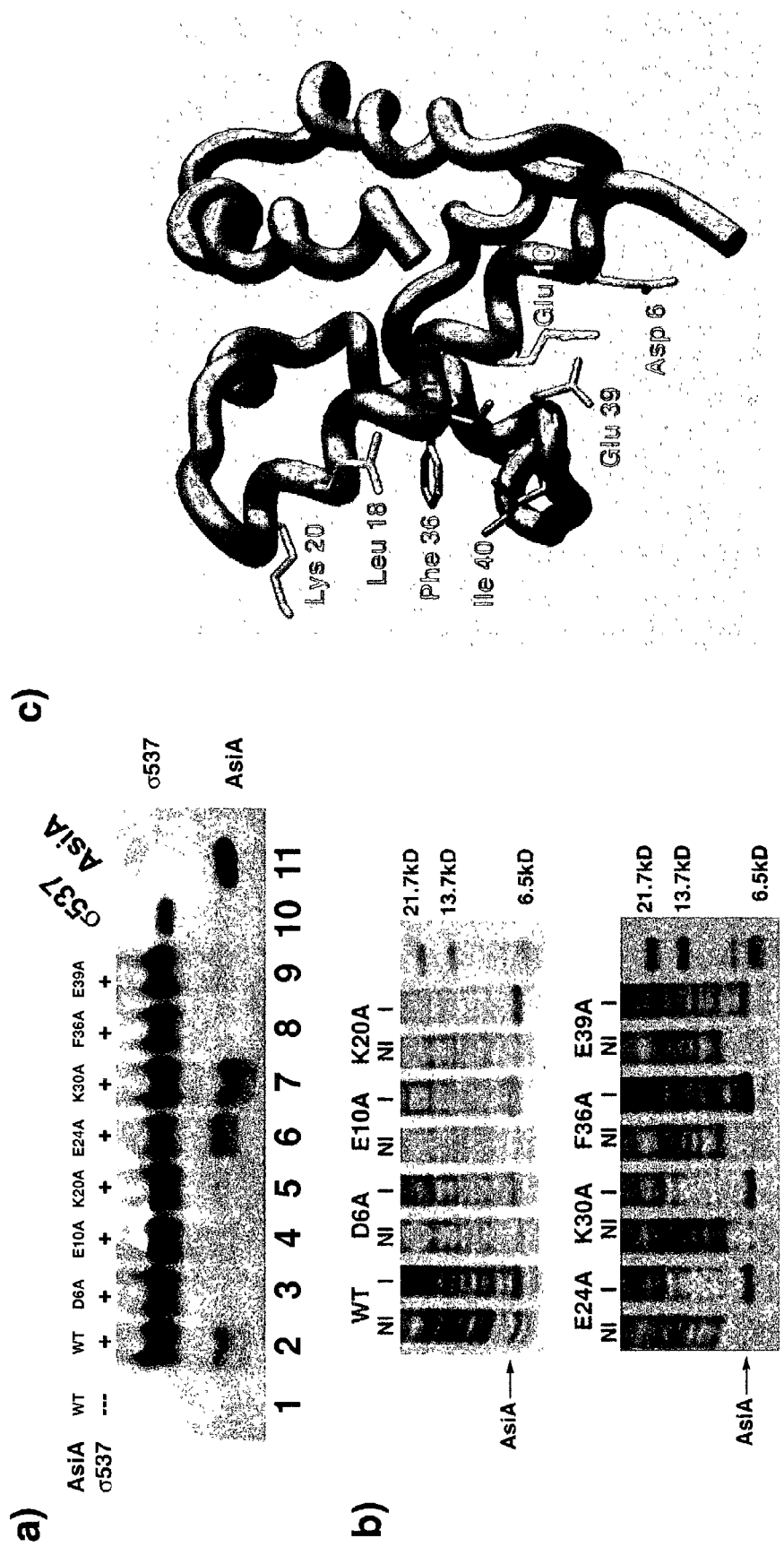
FIG. 6: Mutagenesis of the AsiA homodimer interface. A) The indicated mutant proteins (lanes 2–9) were analyzed for their ability to bind σ537 immobilized on chelating sepharose 4B. Lane 1 represents a pulldown assay with beads alone (i.e. Ni$^{2+}$ beads lacking σ537). Lane 10 represents purified σ537 that has not been exposed to AsiA. Lane 11 is purified wildtype AsiA that has not been exposed to σ537. Alanine substitution of charged residues which reside at the AsiA homodimer interface (Asp 6, Glu 10, Glu 39) result in mutant proteins which fail to bind σ537. Alanine substitution at two other residues, Glu 24 and Lys 30, retain the ability to bind AsiA in this assay. B) Expression of wildtype and mutant AsiAs. Uninduced (NI) and induced (I) expression of wildtype and mutant AsiAs visualized by coomassie staining. The position of the induced band representing the wildtype or mutant proteins is indicated. D) Mapping of the heterodimer interface onto the AsiA monomer structure. Red residues (Thr 13, Leu 18, Ala 35, Ile 40) display intermolecular NOEs to SR4 in an AsiA/σ537 complex. Green residues (Asp 6, Glu 10, Lys 20, Phe 36, Glu 39) fail to bind SR4 in a pulldown assay when mutated to alanine. Ala 35 is obscured in this view and cannot be seen.
Figure 7:
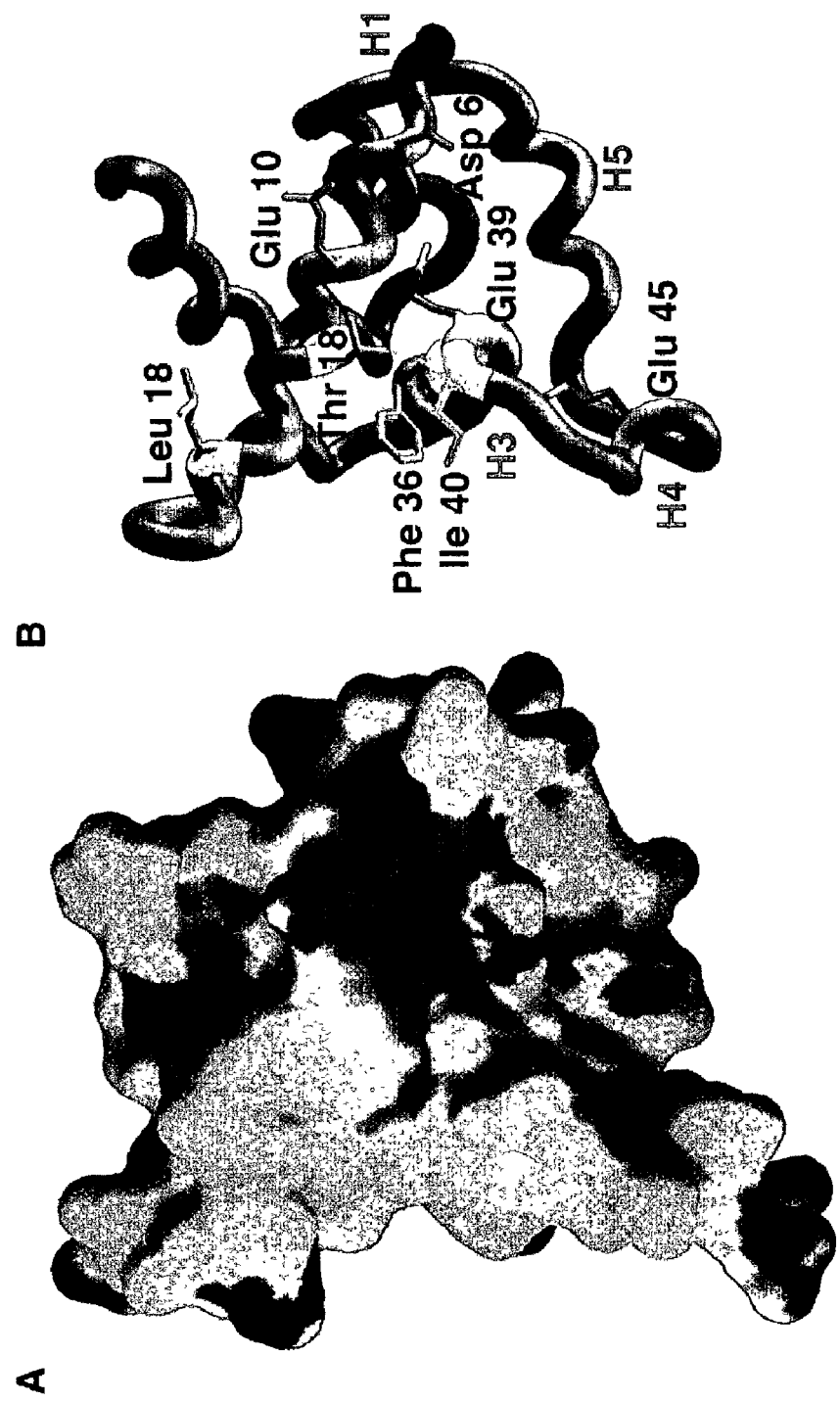
FIG. 7: Characteristics of SR4 binding surface of AsiA. A) Electrostatic potential map (drawn at ±9 kT) of the AsiA monomer viewed from the homodimer interface (Nicholls et al., 1991, Proteins 11: 281–296). Negatively charged surfaces are shown in red and positively charged surfaces in purple. B) The negative patch seen in the center of the electrostatic surface is created by a collection of acidic residues (Asp 6, Glu 10, Glu 39 and Glu 45). These residues are hypothesized to be at least partially buried at the AsiA/SR4 interface. Hydrophobic amino acids which also make-up part of the SR4 binding surface are shown in yellow.
Figure 9:
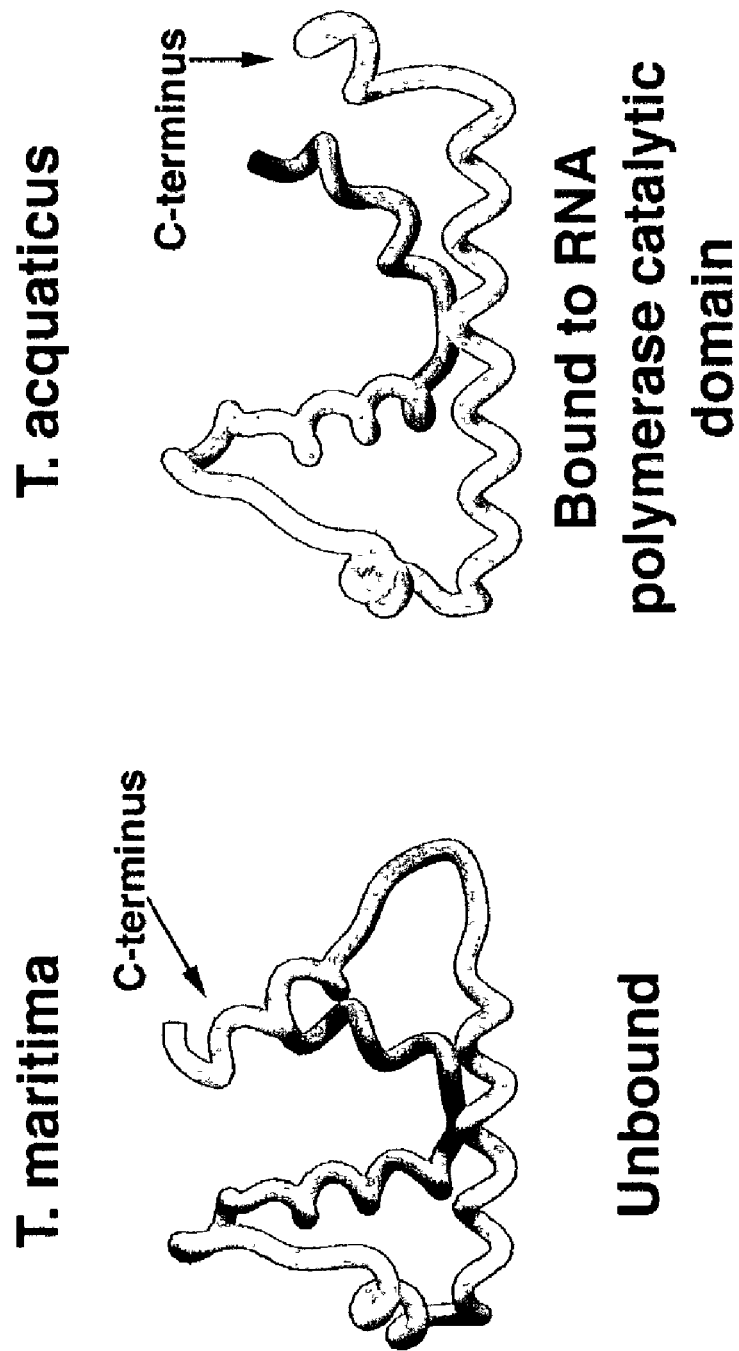
FIG. 9: Conformation of the AsiA target subunit SR4 from the sigA protein of *Thermotoga maritima*. The conformation of the AsiA target subunit has been determined in solution by NMR spectroscopy as described under the subheading 'NMR spectroscopy' on page 15 of the present application. The protein backbone is represented as a green 'worm'. The conformation of *T. maritima* SR4 domain (left) as been determined to demonstrate the structure of the AsiA target in solution. Comparison to the structure of the *T. acquaticus* SR4 conformation when SR4 is bound to the catalytic domain of RNA polymerase illustrates that the basic conformation of SR4 is highly conserved, but that the C-terminus of the domain (indicated by arrow) is repositioned between the free and bound states. This suggests that the C-terminus of the protein may have an important role in the function of the domain. The conformation of SR4 in the sigA proteins of *T. thermophilus* (Campbell et al. 2002, Mol. Cell 9: 527–539) and *T. aquaticus* (Vassylyev et al. 2002, Nature 417, 712–719) are very similar to that seen for the *T. maritima* domain, consistent with the extent of amino acid sequence identity found between them (>90% identical in pairwise comparisons).
Figure 10:
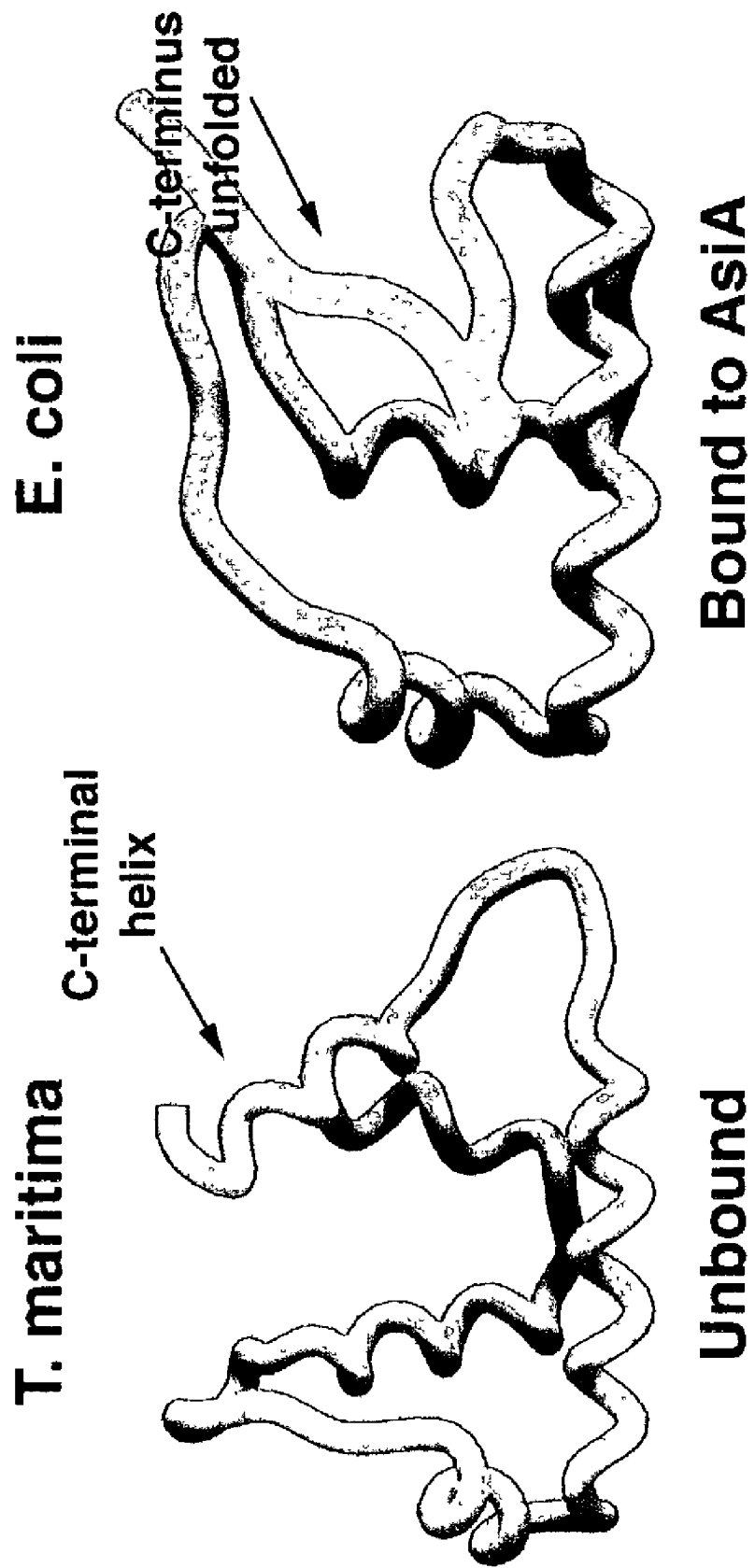
FIG. 10: Unfolding of the SR4 subunit of *Eschericia coli* upon binding AsiA. The conformation of the unbound *T. maritima* SR4 subunit (left) is compared to that of the *E. coli* subunit when bound to AsiA. The comparison reveals that AsiA unfolds the C-terminus of the SR4 subunit is unfolded upon binding AsiA. Thus, AsiA alters the conformation of an essential structural element of SR4 upon binding.
Figure 11A:
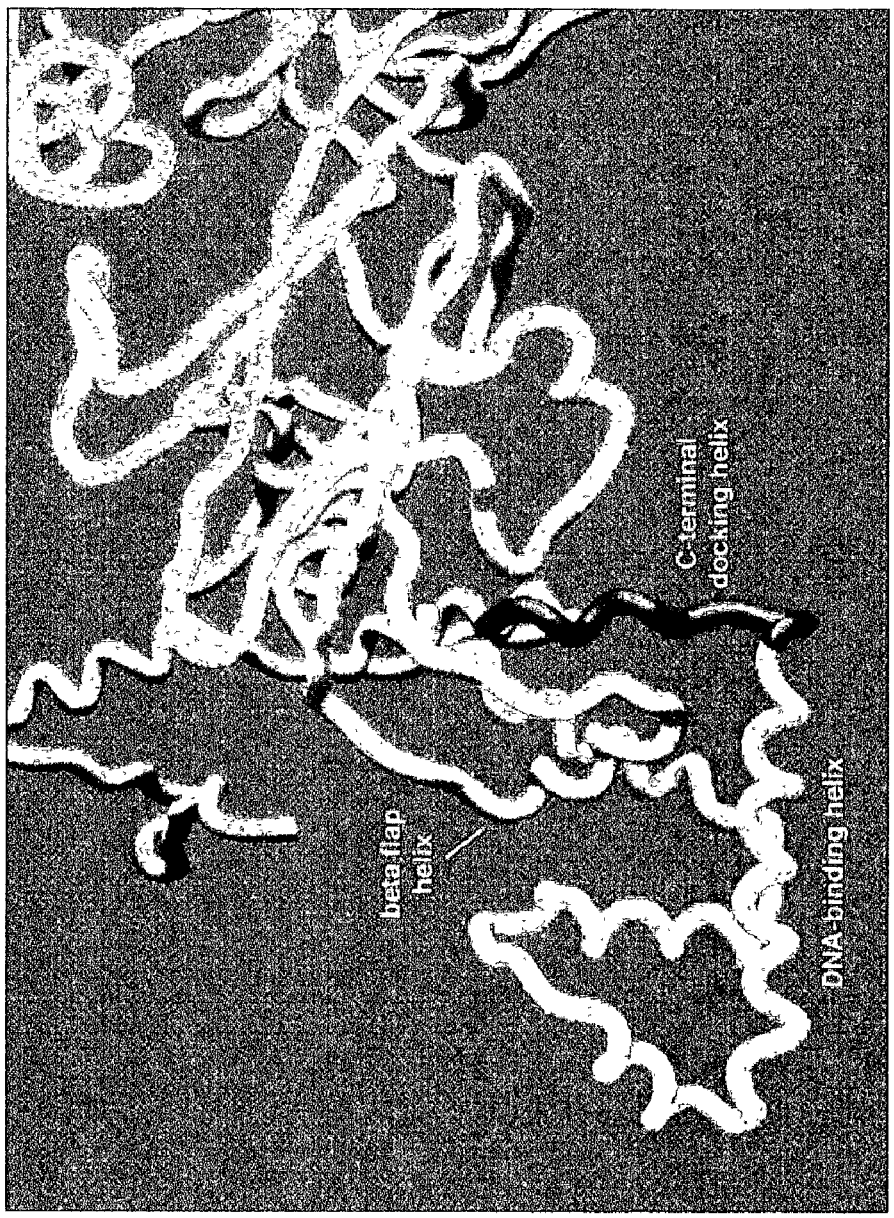
FIG. 11: Unfolding of the SR4 C-terminus by AsiA precludes SR4 recognition of promoter DNA. A) Docking of SR4 into the catalytic domain β subunit. The position of SR4 (pale green and purple) on the surface of the holoenzyme (bright green) is established by the interaction of the β flap helix with SR4 and the docking of the C-terminal helix (purple) of SR4 between two segments of the β subunit, as indicated (Vassylyeva et al 2002, Nature 417: 712–719). B) The unfolding of the C-terminus of SR4 dislodges the domain from its normal docking environment within the RNA polymerase catalytic domain. Normally, the RNA polymerase β-subunit flap helix engages SR4 to hold it in the correct spatial arrangement for recognition of −35 promoter DNA. The unfolding of the C-terminus of SR4 and the concomitant conformational changes in the domain dislodges SR4 from its normal docking site on the enzyme as shown. The result is to displace SR4 from its position within the enzyme, precluding recognition of promoter DNA at −35. This observation provides a molecular explanation for the inability of RNA polymerase to recognize promoter DNA when bound to AsiA. Thus, AsiA represses bacterial gene expression by precluding the ability of RNA polymerase to recognize promoter DNA. Although not shown in this figure, AsiA binds in the pocket that would normally be bound by the β subunit flap.
Figure 11B:
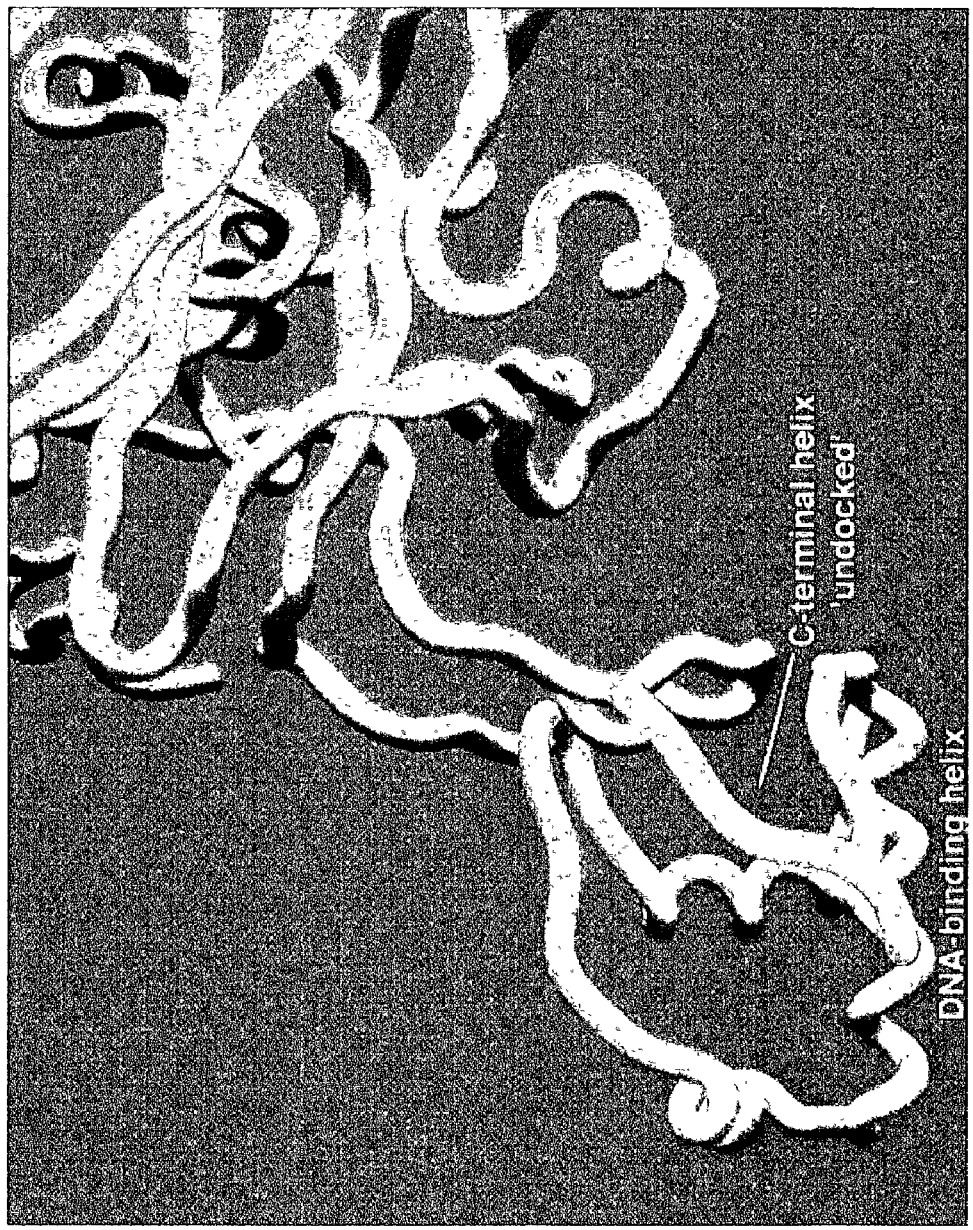

The presumptive AsiA/SR4 interface was further analyzed by site-directed mutagenesis. Alanine substitution at Asp 6, Glu 10, Lys 20, Phe 36 and Glu 39, all residues which participate in the homodimer interface, appear to completely disrupt the interaction with SR4 in a pulldown assay (FIG. 6A) employing crude *E. coli* extracts of the AsiA proteins (FIG. 6B). Several of these positions, Glu 10, Lys 20, Phe 36, also displayed significant changes in chemical shift by NMR 'footprinting' (FIG. 3B), although it is not theoretically possible to correlate the extent of the NMR chemical shift changes with the relative binding affinity seen for these mutants in a pulldown assay. Alanine mutagenesis at Glu 24 and Lys 30 does not appear to disrupt binding with SR4 in this assay (FIG. 6A). In accordance with the mutagenesis data, these positions were relatively unperturbed by 'footprinting' analysis (FIG. 3B).

What is claimed is:

1. A method for identifying an agent that inhibits or alters bacterial gene transcription in a target bacterium comprising the steps of:

i) identifying sites on a SR4 domain of a homologous sigma factor in the target bacterium that correspond with the sites on the SR4 domain of *E. coli* $E\sigma^{70}$ that interact with AsiA and result in repression of the activity of $E\sigma^{70}$ toward bacterial promoters, wherein said sites on said SR4 domain of *E. coli* $E\sigma^{70}$ comprise the amino acid sequence of SEQ ID NO: 1;

ii) modeling agents based in (i) above that bind to the SR4 domain of the homologous sigma factor of the target bacterium;

iii) synthesizing and evaluating said agents in vitro for enhanced binding to said SR4 domain;

iv) adding or combining said agents with a target bacterium; and v) selecting an agent among those in (iv) which inhibit or alter gene expression in said target bacterium.

2. The method of claim 1 wherein said agent is a protein, a peptide, or a small-molecule compound, such as an organic compound.

3. The method of claim 1 wherein said sites on the SR4 domain of *E. coli* $E\sigma^{70}$ that interact with AsiA and result in alteration of the activity of $E\sigma^{70}$ toward bacterial promoters are in helices H1 and H3 of AsiA.

4. The method of claim 3 wherein said sites are about in the first 40 amino acid residues of AsiA.

5. The method of claim 4 wherein said sites are among amino acids 3–20 and 33–44 of AsiA.

6. The method of claim 5 wherein said sites are Asp 6, Glu 10, Ile 11, Ile 12, Thr 13, Leu 18, Ala 35, Phe 36, Glu 39, or Ile 40 of AsiA.

7. The method of claim 1 wherein said bacterium is a plant or animal pathogen.

8. The method of claim 7 wherein said plant pathogen is *Erwinia amylovora, Clavibacter michiganense, Erwinia carotovora, Pseudomonas solanacearum, Pseudomonas syringae*, or *Xanthomonas* spp.

9. The method of claim 7 wherein said animal pathogen is a mammalian pathogen.

10. The method of claim 9 wherein said mammalian pathogen is a human pathogen.

11. The method of claim 10 wherein said human pathogen is *Escherichia coli, Staphylococcus aureus, Streptococcus pyogenes, Bacillus anthracis, Klebsiella pneumoniae, Mycobaterium tuberculosis, Mycobacterium leprae, Vibrio cholerae, Neisseria gonorrhoeae, Treponema pallidum, Pseudomonas aeruginosa, Leigonella* spp., *Yersinia pestis, Bordetella pertussis, Salmonella* spp., *Clostridium tetani, Shigella dysinteriae*, or *Corynebacterium diphtheriae.*

12. A method of screening for SR4 antagonists, comprising:

(a) contacting a test molecule with the SR4 domain of $E\sigma^{70}$, wherein said SR4 domain comprises the amino acid sequence of SEQ ID NO: 1, or with an SR4 fragment, and (b) determining whether the test molecule binds the SR4 domain or the SR4 fragment, wherein the test molecule binding the SR4 domain or the SR4 fragment inhibits microbial growth.

* * * * *

SEQUENCE LISTING

<160> NUMBER OF SEQ ID NOS: 1

<210> SEQ ID NO 1
<211> LENGTH: 81
<212> TYPE: PRT
<213> ORGANISM: Eubacteria

-continued

```
<400> SEQUENCE: 1

Asp Ser Ala Thr Thr Glu Ser Leu Arg Ala Ala Thr His Asp Val Leu
 1              5                   10                  15

Ala Gly Leu Thr Ala Arg Glu Ala Lys Val Leu Arg Met Arg Phe Gly
            20                  25                  30

Ile Asp Met Asn Thr Asp His Thr Leu Glu Glu Val Gly Lys Gln Phe
        35                  40                  45

Asp Val Thr Arg Glu Arg Ile Arg Gln Ile Glu Ala Lys Ala Leu Arg
    50                  55                  60

Lys Leu Arg His Pro Ser Arg Ser Glu Val Leu Arg Ser Phe Leu Asp
65                  70                  75                  80

Asp
```